(12) United States Patent
Veasey et al.

(10) Patent No.: US 9,375,535 B2
(45) Date of Patent: Jun. 28, 2016

(54) DRIVE MECHANISM FOR A DRUG DELIVERY DEVICE

(75) Inventors: Robert Veasey, Leamington Spa (GB); Simon Lewis Bilton, Leamington Spa (GB); Christopher Jones, Tewkesbury (GB); Garen Kouyoumjian, Leamington Spa (GB); Catherine Anne Macdonald, Ashby de la Zouch (GB)

(73) Assignee: SANOFI-AVENTIS DEUTSCHLAND GMBH, Frankfurt am Main (DE)

( * ) Notice: Subject to any disclaimer, the term of this patent is extended or adjusted under 35 U.S.C. 154(b) by 1126 days.

(21) Appl. No.: 13/497,378

(22) PCT Filed: Sep. 29, 2010

(86) PCT No.: PCT/EP2010/064407
§ 371 (c)(1),
(2), (4) Date: Sep. 12, 2012

(87) PCT Pub. No.: WO2011/039216
PCT Pub. Date: Apr. 7, 2011

(65) Prior Publication Data
US 2013/0006193 A1 Jan. 3, 2013

(30) Foreign Application Priority Data
Sep. 30, 2009 (EP) .................................... 09171748

(51) Int. Cl.
| | | |
|---|---|---|
| *A61M 5/00* | (2006.01) | |
| *A61M 5/315* | (2006.01) | |
| A61M 5/24 | (2006.01) | |
| A61M 5/31 | (2006.01) | |

(52) U.S. Cl.
CPC ......... *A61M 5/3158* (2013.01); *A61M 5/31543* (2013.01); *A61M 5/31555* (2013.01);
(Continued)

(58) Field of Classification Search
CPC ..................... A61M 5/14244; A61M 5/31551; A61M 5/31575; A61M 5/24; A61M 5/31558
USPC .................. 604/207–211, 232, 218
See application file for complete search history.

(56) References Cited

U.S. PATENT DOCUMENTS

| | | | | |
|---|---|---|---|---|
| 5,304,152 A | * | 4/1994 | Sams ................ | A61M 5/31553 604/207 |
| 5,599,314 A | | 2/1997 | Neill | |

(Continued)

FOREIGN PATENT DOCUMENTS

EP 1923083 5/2008
(Continued)

OTHER PUBLICATIONS

Japanese Office Action issued for JP App. No. 2012-531384, mailed Jul. 15, 2014.
(Continued)

*Primary Examiner* — Phillip Gray
(74) *Attorney, Agent, or Firm* — McDonnell Boehnen Hulbert & Berghoff LLP

(57) ABSTRACT

According to one aspect, a resettable drive assembly for a drug delivery device is provided for. The resettable drive assembly may comprise a housing having a proximal end and a distal end, a piston rod being rotatable with respect to the housing and being axially displaceable with respect to the housing between a proximal start position and a distal end position, a drive member for distally displacing the piston rod towards the end position when dispensing a dose, and a stop member. The drive assembly may be configured such that the drive member is operable to interact with the piston rod for forming an unlockable first interlock, the first interlock being operable to block proximal movement of the piston rod with respect to the drive member. The drive assembly may be configured such that the stop member is operable to interact with the piston rod for forming an unlockable second interlock, the second interlock being operable to block proximal movement of the piston rod with respect to the housing. The drive assembly may be configured such that, when the drive assembly is in a drive mode, the first and second interlocks are locked such that proximal movement of the piston rod from the end position to the start position is prevented by the first interlock and the second interlock. The drive assembly may be configured such that, for switching the drive assembly from the drive mode to a reset mode, the piston rod is rotatable with respect to the drive member for unlocking the first interlock and the stop member and the piston rod are rotatable with respect to each other for unlocking the second interlock. The drive assembly may be configured such that, when the drive assembly is in the reset mode, the first interlock and the second interlock are unlocked such that proximal movement of the piston rod to the start position is allowed. Further, a drug delivery device and a use of a spring are provided for.

13 Claims, 15 Drawing Sheets

(52) U.S. Cl.
CPC ............. *A61M 5/24* (2013.01); *A61M 5/31541* (2013.01); *A61M 5/31556* (2013.01); *A61M 2005/2407* (2013.01); *A61M 2005/2477* (2013.01); *A61M 2005/3126* (2013.01)

(56) References Cited

U.S. PATENT DOCUMENTS

| | | | |
|---|---|---|---|
| 6,663,602 B2* | 12/2003 | Møller | A61M 5/24 222/390 |
| 2002/0095120 A1 | 7/2002 | Larsen et al. | |
| 2007/0142789 A1 | 6/2007 | Fisher et al. | |

FOREIGN PATENT DOCUMENTS

| EP | 2078536 | 7/2009 |
|---|---|---|
| WO | 94/07562 | 4/1994 |
| WO | 2005/102420 | 11/2005 |
| WO | 2006/130098 | 12/2006 |
| WO | 2008/058668 | 5/2008 |
| WO | 2009/007305 | 1/2009 |
| WO | 2010/029043 | 3/2010 |

OTHER PUBLICATIONS

Partial European Search Report for EP Application No. 09171748, completed Mar. 24, 2010.
International Search Report for Int. App. No. PCT/EP2010/064407, completed Apr. 6, 2011.
International Preliminary Report on Patentability for International App. No. PCT/EP2010/064407, issued Apr. 3, 2012.
Extended European Search Report for divisional European patent application 12 198 968.5 of parallel European application 10 759 643.9, issued Feb. 28, 2013.

* cited by examiner

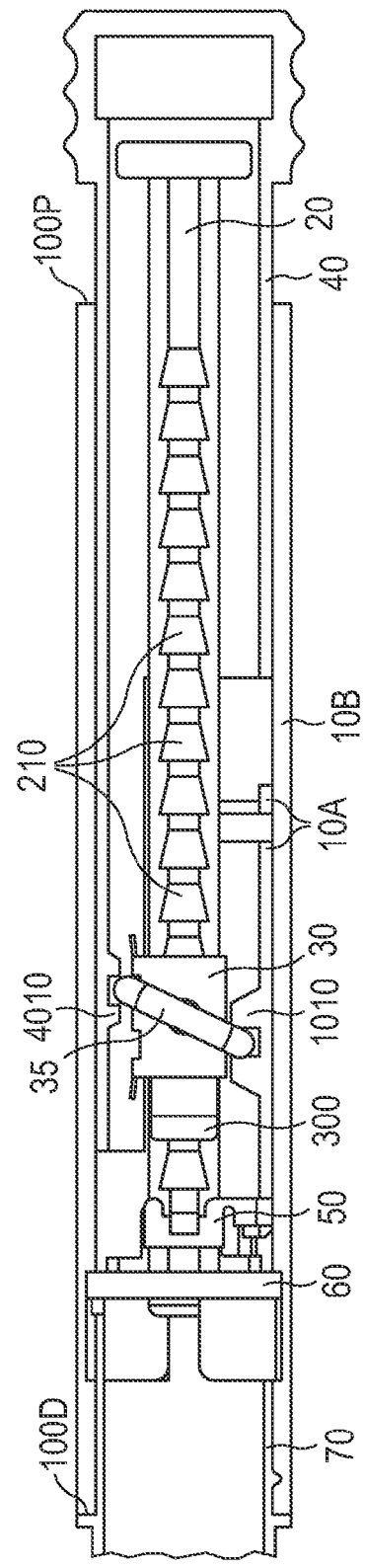
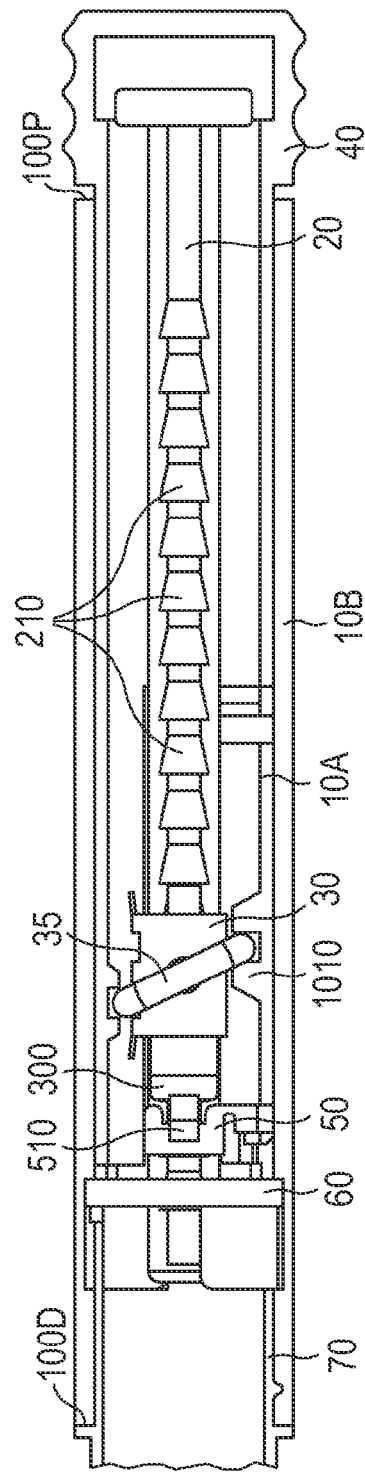
FIG 1B
FIG 1C

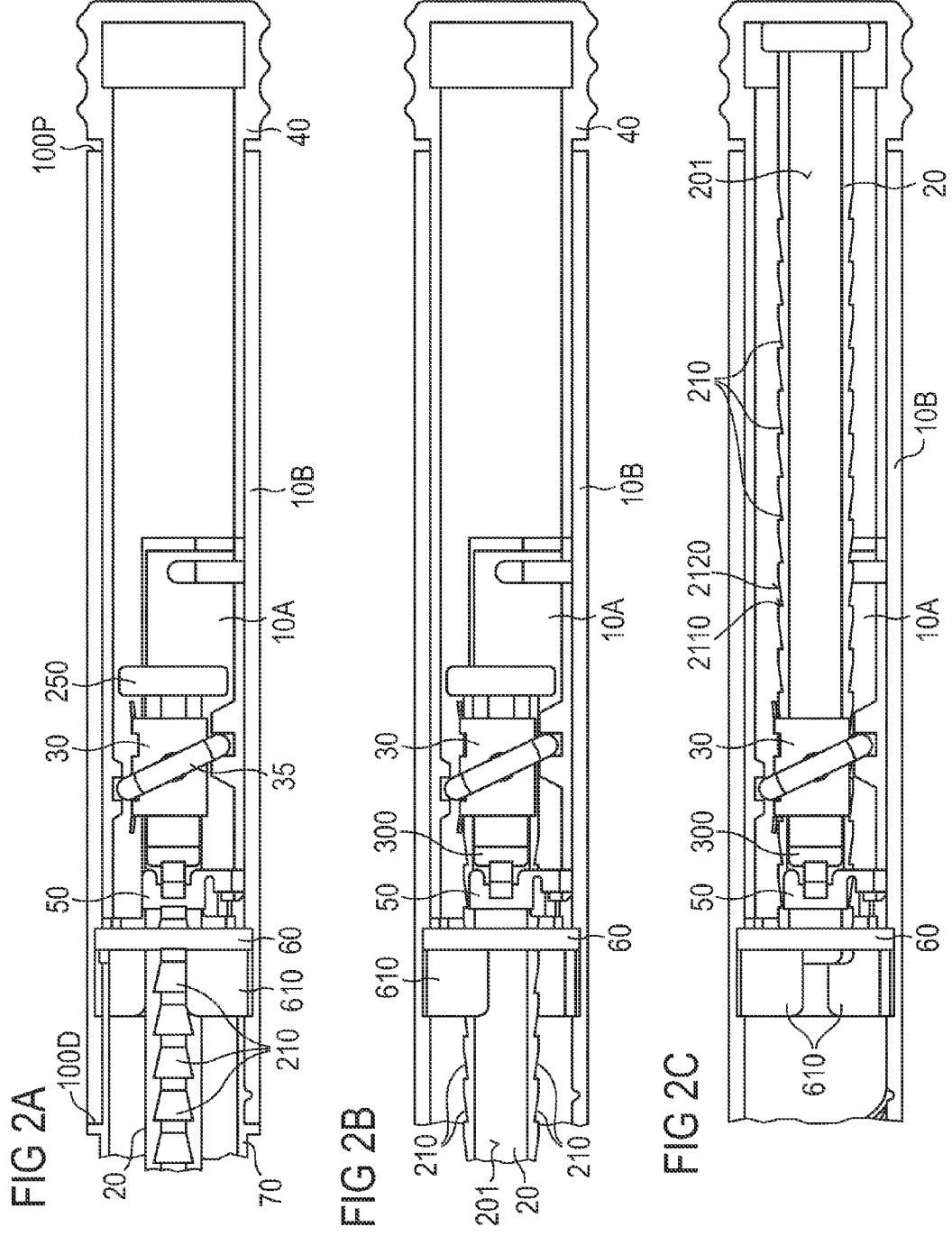

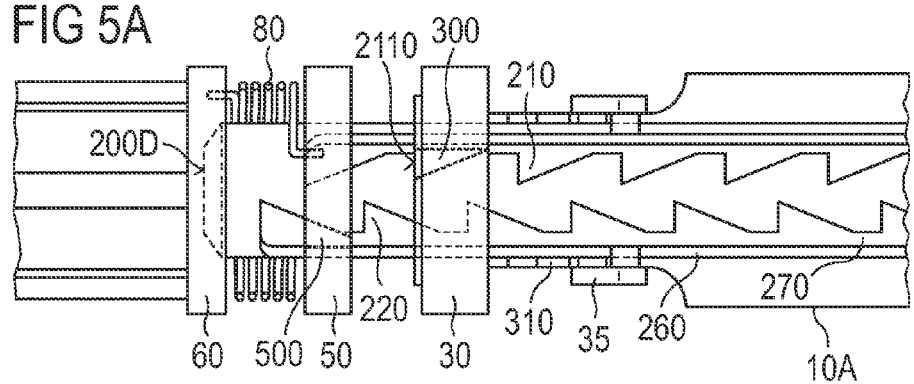
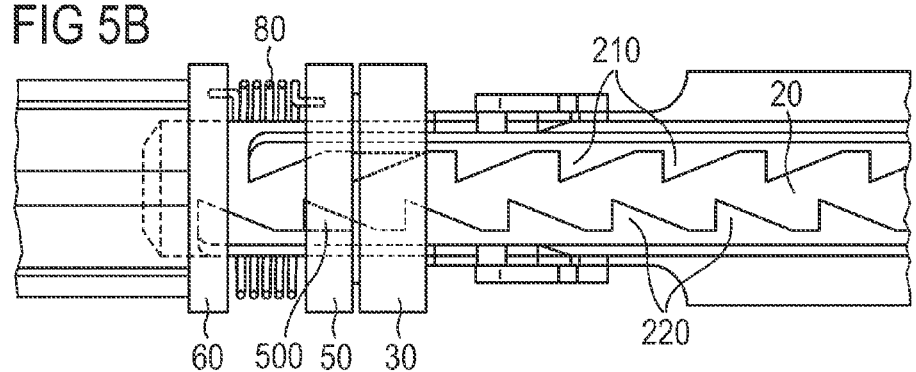
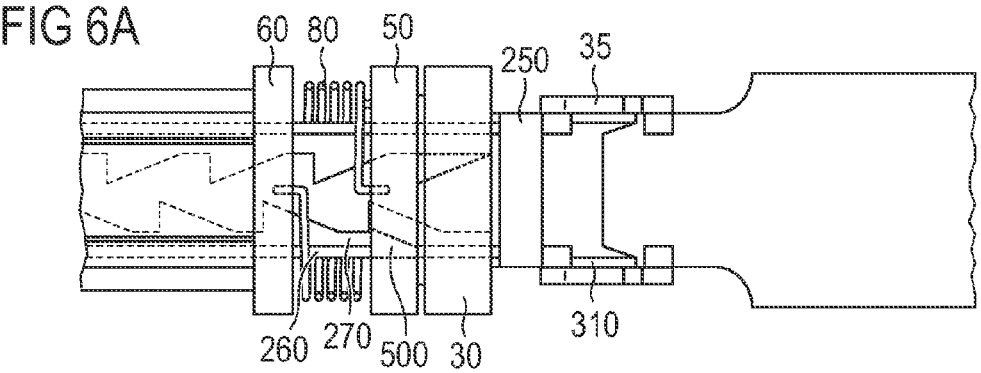
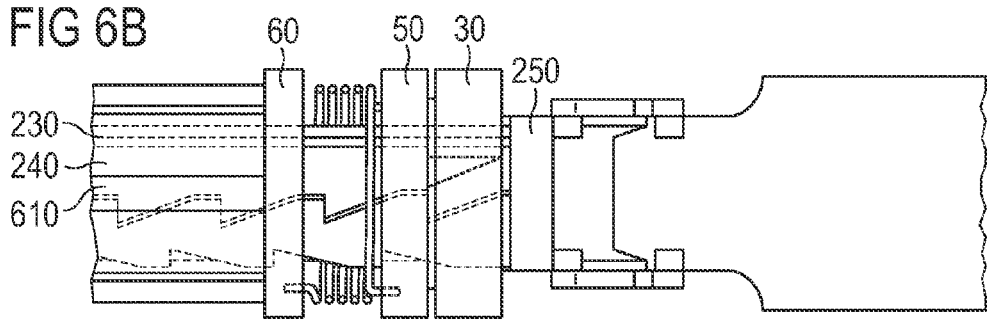

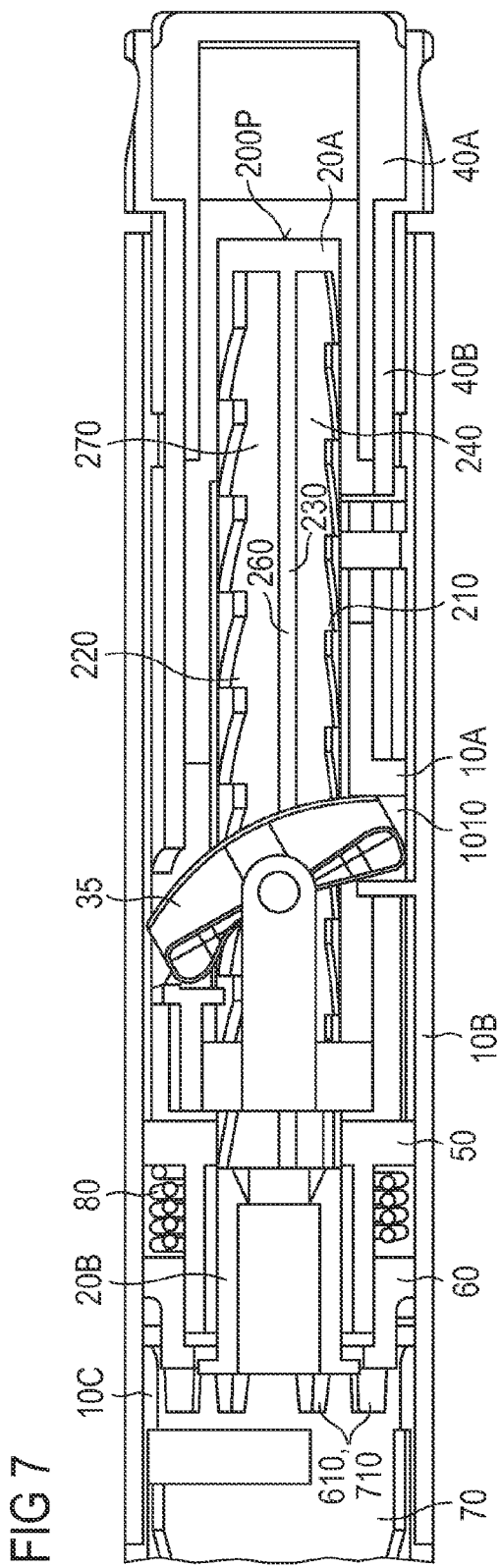

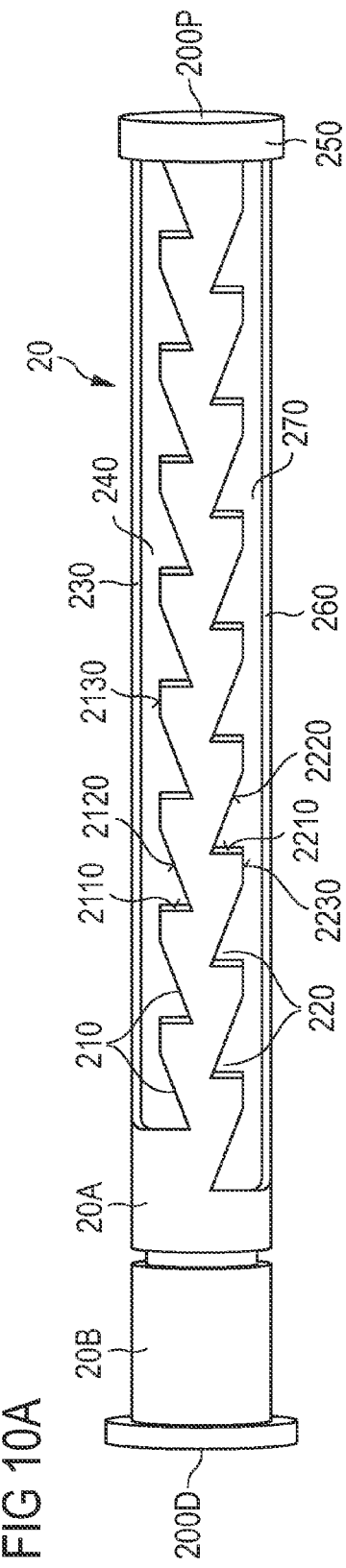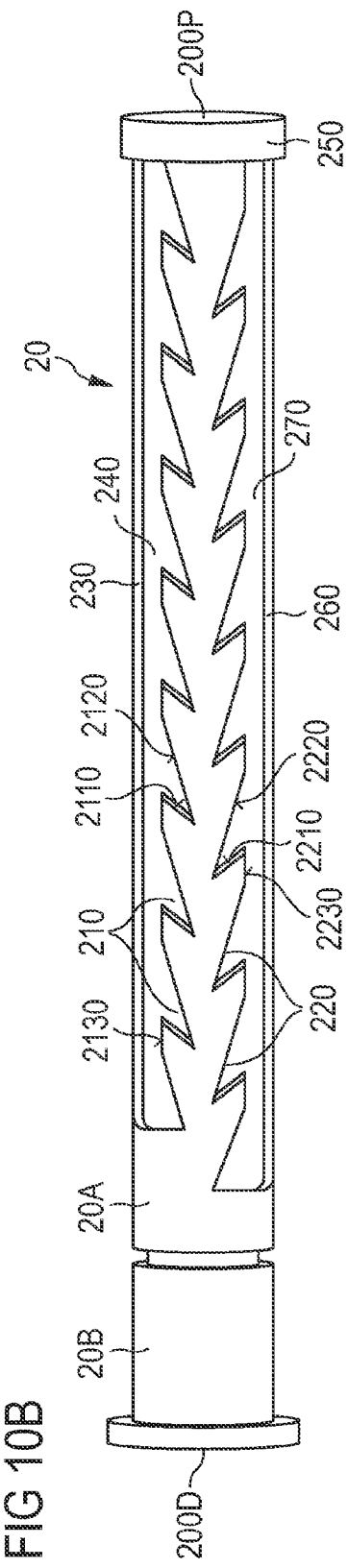

DRIVE MECHANISM FOR A DRUG DELIVERY DEVICE

CROSS REFERENCE TO RELATED APPLICATIONS

The present application is a U.S. National Phase Application pursuant to 35 U.S.C. §371 of International Application No. PCT/EP2010/064407 filed Sep. 29, 2010, which claims priority to European Patent Application No. 09171748.8 filed on Sep. 30, 2009. The entire disclosure contents of these applications are herewith incorporated by reference into the present application.

FIELD OF INVENTION

The present disclosure relates to a piston rod, a drive assembly, a drug delivery device, and to the use of a spring.

BACKGROUND

EP 1923083 A1 discloses drive mechanisms for use in drug delivery devices.

SUMMARY

It is an object of the present disclosure to provide for a novel piston rod, drive assembly, drug delivery device, and/or use of a spring.

According to at least one aspect, a piston rod is provided for. The piston rod may be flexible or not. It may be a simple rod, a lead screw, a rack and pinion system, a worm gear system, or the like. The piston rod may have a circular or a non-circular cross-section. It may be made of any suitable material known by a person skilled in the art and may be of unitary or multi-part construction. The piston rod may have a proximal end, a distal end, and a main longitudinal axis extending between the proximal end and the distal end.

According to at least one aspect, the piston rod has one or more rows of axially spaced ribs and/or indentations. The ribs or indentations preferably form one or more rows of ratchet pockets. The row(s) of ratchet pockets may extend in an axial or substantially axial direction. A row of ratchet pockets which extends in an axial or substantially axial direction is subsequently denoted as an axial row of ratchet pockets.

According to at least one aspect, each ratchet pocket tapers in a radial direction towards the longitudinal axis of the piston rod. Expediently, in this case, the ratchet pockets are configured for interacting with a radially displaceable pawl element.

According to at least one aspect, the piston rod comprises at least one first ratchet pocket with a proximal sidewall and a distal sidewall. The proximal sidewall and the distal sidewall may delimit the first ratchet pocket axially and, preferably, such that the first ratchet pocket tapers in a first angular direction with respect to the longitudinal axis. The first ratchet pocket is, in particular, configured for interacting with a pawl element which is rotatable around the longitudinal axis. Preferably, a distance between the longitudinal axis and the pawl element is fixed or essentially fixed in this embodiment.

Preferably, the piston rod comprises one or more rows of first ratchet pockets. The respective row may be oriented axially, in particular extend in an axial or at least substantially axial direction. According to at least one aspect, axially successive first ratchet pockets of at least one row are axially spaced apart from each other.

According to at least one aspect, the piston rod comprises a first protrusion. The first protrusion may extend axially or at least substantially axially. The first protrusion may define a channel in cooperation with the first ratchet pocket, and, in particular, in cooperation with the row or one of the rows of first ratchet pockets. The first ratchet pocket(s) may form a bulge of the channel. The channel is preferably configured such that the pawl element is movable from one first ratchet pocket of the row to a subsequent first ratchet pocket of the axial row through the channel. The channel may extend axially or at least substantially axially along the piston rod. The first protrusion may extend along a plurality, preferably along all, first ratchet pockets of the respective row.

According to at least one aspect, the piston rod comprises at least one second ratchet pocket. The second ratchet pocket is preferably angularly offset from the first ratchet pocket. The second ratchet pocket has a proximal sidewall and a distal sidewall which delimit the second ratchet pocket axially and, preferably, such that the second ratchet pocket tapers in a second angular direction with respect to the axis. The second angular direction may be opposite to the first angular direction. Preferably, the piston rod comprises one or more rows of second ratchet pockets. The respective row may be oriented axially. According to one aspect, axially successive second ratchet pockets of at least one row are axially spaced apart from each other.

According to at least one aspect, the second ratchet pocket is axially offset from the first ratchet pocket. In particular first ratchet pockets and second ratchet pockets are axially staggered such that one, in particular one and only one, second ratchet pocket is axially arranged between each pair of directly axially successive first ratchet pockets.

According to at least one aspect, the piston rod has a ridge. The ridge may be oriented axially. The ridge may comprise a first set of indentations representing the row or one of the rows of first ratchet pockets. The ridge may comprise a second set of indentations representing the row or one of the rows of second ratchet pockets.

According to at least one aspect, the piston rod comprises a second protrusion. The second protrusion may extend axially or at least substantially axially. The second protrusion may define a channel in cooperation with the second ratchet pocket or in cooperation with the row or one of the rows of second ratchet pockets. The second ratchet pocket(s) form(s) a bulge of the channel. According to at least one aspect, the first and second protrusions are comprised by one continuous web on the piston rod.

Similar to the first ratchet pocket(s), the second ratchet pocket(s) may be configured for interacting with a further pawl element. The further pawl element may be rotatable around the longitudinal axis of the piston rod. In particular, the further pawl element is movable from one second ratchet pocket to a subsequent second ratchet pocket of the row or one of the rows of second ratchet pockets through the channel defined by the second protrusion and the second ratchet pockets. The channel may extend axially along the piston rod. The second protrusion may extend along a plurality, preferably all second ratchet pockets of the respective row.

Each of the proximal sidewall and the distal sidewall of a respective first ratchet pocket may, for example, extend in the first angular direction from a respective first edge to a respective second edge. Similarly, each of the proximal sidewall and the distal sidewall of a respective second ratchet pocket may, for example, extend in the second angular direction from a respective first edge to a respective second edge.

The distance between the first edge of the proximal sidewall and the first edge of the distal sidewall may be greater than the distance between the second edge of the proximal sidewall and the second edge of the distal sidewall. According to at least one aspect, the second edge of the proximal sidewall and the second edge of the distal sidewall may coincide such that they, in particular, form a common edge of the pocket. The first and/or second edges of the proximal and/or distal sidewalls extend, for example, radially with respect to the longitudinal axis.

According to at least one aspect, the second edge of the proximal sidewall is arranged closer to the distal end of the piston rod than the first edge of the proximal sidewall. The first and the second edge of the distal sidewall may be arranged at the same distance from the proximal end of the piston rod, for example. The first and second ends of the distal sidewall may alternatively be arranged at different distances from the proximal end. For example, the second edge of the distal sidewall is arranged closer to the proximal end of the piston rod than the first edge of the distal sidewall. This may be advantageous for locking the pawl element in the first ratchet pocket with high stability, for example.

According to at least one aspect, the proximal sidewall of the first ratchet pocket is inclined with respect to the longitudinal axis of the piston rod as seen in plan view onto the piston rod and the first ratchet pocket. In particular, an inclination angle of the proximal sidewall may be greater than an inclination angle of the distal sidewall. The distal sidewall may, for example, extend substantially perpendicular with respect to the longitudinal axis. In particular, the first edge of the distal sidewall and the second edge of the distal sidewall are axially spaced apart from each other by a shorter distance than the first edge of the proximal sidewall and the second edge of the proximal sidewall.

According to at least one aspect, a drive assembly is provided for. The drive assembly may be a drive assembly for a drug delivery device.

According to at least one aspect, the drive assembly is a resettable drive assembly. The resettable drive assembly may have a drive mode and a reset mode.

According to at least one aspect, the drive assembly comprises a housing. The housing may have a proximal end and a distal end.

According to at least one aspect, the drive assembly comprises a piston rod, for example a piston rod of the type described above. The piston rod may be axially displaceable with respect to the housing. For example, it may be axially displaceable with respect to the housing between a proximal start position and a distal end position. According to at least one aspect, the piston rod is also rotatable with respect to the housing. In particular, it is rotatable with respect to the housing between a first angular position and a second angular position. Preferably, the drive assembly is configured such that the angular range of motion of the piston rod, in particular between the first and second angular positions, is less than 360°, particularly preferably it is 90° or less.

According to at least one aspect, the drive assembly comprises a drive member. The drive member may be axially displaceable, in particular with respect to the housing and/or with respect to the piston rod. The drive member may be axially displaceable with respect to the housing and rotationally locked with respect to the housing. According to at least one aspect, the drive member comprises a sleeve. A sleeve which has, in particular, a small axial dimension, may also be denoted as a ring. For example, the drive member is a drive sleeve. The piston rod may extend through the sleeve. Preferably, the drive member is configured for distally displacing the piston rod towards the distal end position, in particular for dispensing a dose. According to at least one aspect, the drive member comprises a pawl element for interacting with the row or one of the rows of first ratchet pockets of the piston rod. Preferably, a respective pawl element of the drive member is assigned to each of the rows of first ratchet pockets of the piston rod.

According to at least one aspect, the drive assembly comprises a reset member. The reset member may be rotatable with respect to the housing. According to at least one aspect, the reset member is releasably rotationally lockable, in particular releasably engageable, with the housing. The drive assembly may be configured such that the reset member is operable to retain the drive assembly in the reset mode when it is engaged with the housing.

According to at least one aspect, the drive assembly comprises a detachable member. The detachable member may be configured for being detachably connected to the housing. The detachable member may be one of a cartridge and a cartridge holder. The cartridge may comprise a piston. The piston rod may be configured for distally displacing the piston, for example for dispensing a dose, in particular a dose of a liquid drug, from the cartridge.

According to at least one aspect, the drive assembly comprises a first diverter element. The first diverter element may be comprised by the reset member, the detachable member or the housing, for example. The drive assembly, in particular the reset member, the detachable member or the housing, may also have a second diverter element.

According to at least one aspect, the first diverter element is a first ramp which may, for example, be comprised or formed by a proximal end of the detachable member or the reset member. The second diverter element may, for example, be a second ramp which may, for example, be comprised or formed by a proximal end of the detachable member or the reset member. The first ramp and, if applicable, the second ramp each have a proximal end and a distal end. In particular when both of the first ramp and the second ramp are comprised by the reset member or the detachable member, the proximal end of the first ramp may be connected to the proximal end of the second ramp.

According to at least one aspect, the drive assembly comprises a rotational bias member. In one embodiment, the rotational bias member comprises a sleeve. The piston rod may extend through the sleeve. According to at least one aspect, the rotational bias member is rotatable with respect to the housing. The rotational bias member may be operable to transfer a resilient bias to the piston rod. According to at least one aspect, the rotational bias member comprises a pawl element for interacting with the row or one of the rows of second ratchet pockets of the piston rod. Preferably, a respective pawl element is assigned to each of the rows of second ratchet pockets of the piston rod.

The drive assembly may, for example, comprise a resilient member, e.g. a spring. The resilient bias member is preferably operable to generate a resilient bias on the rotational bias member and/or the piston rod. In particular, the drive assembly is operable to transfer the resilient bias generated by the resilient member to the piston rod via the rotational bias member. According to at least one aspect, one end of the resilient member may be firmly connected, in particular fixed, to the rotational bias member. According to at least one aspect, a further end of the resilient member may be firmly connected, in particular fixed, to the reset member or the housing.

According to at least one aspect, the rotational bias member has a first part and a second part. The first part is, for example, axially locked with respect to the housing. The second part is, for example, axially displaceable with respect to the first part and the housing. The second part may be rotationally coupled to the first part. In particular, the second part may be rotationally locked with respect to the first part. The drive assembly may be configured for converting axial movement of the second part with respect to the first part into rotational movement of the first part—and, in particular, of the second part—with respect to the housing.

According to at least one aspect, the drive assembly comprises a stop member. The stop member may be configured for interacting with the piston rod for blocking proximal axial movement of the piston rod with respect to the housing. The stop member may be axially locked with respect to the housing. According to one aspect, the stop member is rotationally locked with respect to the housing. According to another aspect, the stop member is rotatable with respect to the housing. The rotational bias member may be formed by the stop member. In particular, the stop member may be operable to interact with the piston rod for blocking proximal axial movement of the piston rod by means of interacting with the piston rod via the pawl element(s).

According to at least one aspect, a drug delivery device is provided for. The drug delivery device may comprise the drive assembly, in particular the resettable drive assembly.

According to at least one aspect, the drive assembly is configured such that, for setting a dose, the drive member is proximally displaceable with respect to the housing and, preferably, with respect to the piston rod, in particular from a rest position to a dose set position. For dispensing the set dose, the drive member may be distally displaceable with respect to the housing from the dose set position towards the rest position.

Preferably, for dispensing the set dose, the drive member interacts with the piston rod to displace the piston rod distally with respect to the housing. According to at least one aspect, the piston rod is only axially displaced during dispensing of the dose. When the piston rod is only axially displaced, it is in particular not rotated. In one embodiment, the piston rod is displaced distally with respect to the rotational bias member when dispensing the dose.

According to at least one aspect, when setting the dose, the piston rod is rotated in a first rotational direction with respect to the housing and, in particular, the drive member and, subsequent to the rotation in the first rotational direction, the piston rod is rotated in a second rotational direction with respect to the housing and, in particular, the drive member. The first rotational direction may in particular coincide with the first angular direction in which the first ratchet pocket of the piston rod tapers. In this case, the second rotational direction may coincide with the second angular direction in which the second ratchet pocket of the piston rod tapers.

According to at least one aspect, the drive member interacts with the piston rod to convert proximal movement of the drive member with respect to the housing into rotational movement of the piston rod in the first rotational direction with respect to the housing and, in particular, with respect to the drive member. The rotational movement of the piston rod in the first rotational direction may be a movement towards the second angular position. In particular, the piston rod is moved in the first rotational direction towards the second angular position against the resilient bias, which is in particular transferred to the piston rod by the rotational bias member.

For example, the proximal axial movement of the drive member is converted to the rotational movement of the piston rod by means of interaction of one first ratchet pocket of the piston rod with the respective pawl element of the drive member. When the drive member moves proximally with respect to the piston rod and rotates the piston rod in the first rotational direction with respect to the housing and the drive member, the pawl element of the drive member may disengage from the first ratchet pocket by means of the relative movement between the piston rod and the drive member. Thus, the rotation angle of the rotational movement of the piston rod may be determined by an angular extension of the first ratchet pocket.

According to at least one aspect, the rotational bias member may interact with the piston rod such that the piston rod is rotated in the second rotational direction, in particular by means of the resilient bias. The rotation of the piston rod in the second rotational direction with respect to the drive member and the housing may be a rotation towards the first angular position. In one embodiment, the angular range of the rotational motion of the piston rod in the second rotational direction may be limited by the drive member. In particular, the drive member prevents further rotation of the piston rod in the second rotational direction when a first ratchet pocket of the piston rod is in full engagement with the respective pawl element of the drive member.

According to at least one aspect, when setting the dose, the rotational bias member follows the piston rod in the first rotational direction—in particular by means of mechanical interaction between the piston rod an the rotational bias member—when the piston rod rotates in the first rotational direction. In particular, the rotational bias member follows the piston rod in the first rotational direction against the resilient bias. According to at least one aspect, the piston rod additionally or alternatively follows the rotational bias member in the second rotational direction, in particular by means of mechanical interaction between the piston rod and the rotational bias member, when the rotational bias member rotates in the second rotational direction. The rotational bias member may, preferably, rotate in the second rotational direction by means of the resilient bias.

For example, during setting the dose, rotational movement of the rotational bias member in the second rotational direction with respect to the piston rod may be prevented by means of engagement of a second ratchet pocket of the piston rod with a respective pawl element of the rotational bias member. Thus, when the piston rod is rotated in the first rotational direction, it may carry the rotational bias member with it in the first angular direction whereas, in particular, the resilient bias tends to rotate the rotational bias member in the second rotational direction.

According to at least one aspect, when dispensing the set dose, the piston rod interacts with the rotational bias member to transform a distal movement of the piston rod into a rotational movement of the rotational bias member, in particular against the resilient bias. The distal movement of the piston rod may be transformed into a rotational movement of the rotational bias member in the first rotational direction with respect to the piston rod and, in particular, the housing.

According to at least one aspect, the drive assembly is operable to elastically deform the resilient member for increasing the resilient bias when the rotational bias member is rotated in the first rotational direction with respect to the housing. According to at least one aspect, the drive assembly is configured for elastically deforming the resilient member by angularly displacing two opposite ends of the resilient member with respect to each other.

According to at least one aspect, the rotational bias member is operable to elastically deform the resilient member, in particular to compress the resilient member in an axial direction, e.g. by means of axially displacing the second part of the rotational bias member with respect to the first part of the rotational bias member.

According to at least one aspect, the drive member is operable to interact with the piston rod for forming a first interlock. The first interlock may be operable to block proximal movement of the piston rod with respect to the drive member. According to at least one aspect, the drive member is coupleable to the piston rod by means of the first interlock such that the drive member is operable to displace the piston rod distally for dispensing a dose. In particular, the first interlock represents a clutch between the piston rod and the drive member which may be configured such that, in particular when the drive assembly is in the drive mode, the piston rod follows distal movement of the drive member and the piston rod does not follow proximal movement of the drive member.

According to at least one aspect, the stop member and/or the rotational bias member is operable to interact with the piston rod for forming a second interlock. The second interlock may, in particular, be operable to block proximal movement of the piston rod with respect to the housing. The second interlock prevents the piston rod from moving proximally when a force in the proximal direction is exerted on the piston rod, for example by the drive member during setting the dose.

For example, proximal axial movement of the piston rod with respect to the housing is blocked by the second interlock by means of interaction of the piston rod with the stop member or the rotational bias member via the row or at least one row of ratchet pockets, in particular second ratchet pockets, of the piston rod.

According to at least one aspect, the second interlock is operable to prevent proximal movement of the piston rod to the proximal start position, starting, for example, from the distal end position. According to at least one aspect, the axial range of motion of the drive member with respect to the housing is limited such that proximal movement of the piston rod with respect to the housing from the distal end position to the proximal start position is prevented by the first interlock, in particular in cooperation with an interaction of the drive member with the housing.

The term "to block proximal movement" shall preferably denote a configuration where the piston rod has a plurality of axially successive block positions, starting from which the piston rod cannot be moved in the proximal direction on account of the first or second interlock, respectively. If the piston rod is in an axial position which is between two subsequent block positions, the respective interlock may allow proximal movement of the piston rod to the next block position. For example, the first and/or second interlock may be designed in a ratchet-like fashion, in particular by means of the pawl elements of the drive member and the rotational bias member, respectively, and the respective rows of ratchet pockets.

For example, for forming the first interlock, the piston rod has a row of ratchet pockets and the drive member is configured for interacting with the row of ratchet pockets for blocking proximal movement of the piston rod with respect to the drive member. According to at least one aspect, the drive member comprises a pawl element which is configured for engaging with one ratchet pocket. In one embodiment, the ratchet pockets may be tapering in a radial direction towards the longitudinal axis of the piston rod. In another embodiment, the row of ratchet pockets is a row of first ratchet pockets, the first ratchet pockets tapering in the first angular direction, as described above.

According to one aspect, for forming the second interlock, the rotational bias member and/or the stop member is configured for interacting with the same row of ratchet pockets with which the drive member interacts. The rotational bias member and/or the stop member may also be configured for interacting with an additional row of ratchet pockets. For example, the rotational bias member and/or the stop member is configured for interacting with a row of second ratchet pockets which taper in the second angular direction, as described above. According to at least one aspect, the rotational bias member and/or the stop member comprises a pawl element which is configured for engaging one of the ratchet pockets.

According to at least one aspect, when dispensing the set dose, the rotational bias member is rotated in the first rotational direction by means of interaction with the piston rod, in particular against the resilient bias. The rotational bias member may be rotated in the first rotational direction for disengaging one of the ratchet pockets, in particular one of the second ratchet pockets.

For example, the distal axial movement of the piston rod is converted to the rotational movement of the rotational bias member by means of interaction of one second ratchet pocket of the piston rod with the respective pawl element of the rotational bias member. When the piston rod moves distally with respect to the rotational bias member and rotates the rotational bias member in the first rotational direction with respect to the housing and the piston rod, the pawl element of the rotational bias member may disengage from the second ratchet pocket by means of the relative movement between the piston rod and the rotational bias member. Thus, the rotation angle of the rotational movement of the rotational bias member may be determined by an angular extension of the second ratchet pocket.

Subsequent to the rotation in the first rotational direction, the rotational bias member may be rotated in the second rotational direction with respect to the housing and the piston rod. The rotational bias member may be rotated in the second rotational direction in particular by means of the resilient bias, for example by means of interaction with the resilient member. In particular, the rotational bias member may be rotated in the second rotational direction for engaging another one of the ratchet pockets, in particular of the second ratchet pockets.

In one embodiment, the angular range of the rotational motion of the rotational bias member in the second rotational direction with respect to the housing may be limited by interaction of the rotational bias member with the housing, in particular via the piston rod and the drive member. For example, the piston rod prevents further rotation of the rotational bias member in the second rotational direction with respect to the piston rod when a second ratchet pocket of the piston rod is in full engagement with the respective pawl element of the rotational bias member. When dispensing the dose, one first ratchet pocket of the piston rod may be fully engaged with a respective pawl element of the drive member which, in turn, may be rotationally locked with respect to the housing.

According to at least one aspect, the first interlock is unlockable and/or the second interlock is unlockable. Unlockable first and/or second interlocks are particularly expedient when the drive assembly is a resettable drive assembly.

According to at least one aspect, when the drive assembly is in the drive mode, the first interlock is locked, in particular such that proximal movement of the piston rod with respect to the drive member is blocked. Proximal movement of the drive member with respect to the piston rod, e.g. for setting a dose, may be allowed by the first interlock. Additionally or alternatively, the second interlock may be locked when the drive assembly is in the drive mode, in particular such that proximal movement of the piston rod with respect to the housing is blocked. Preferably, the first interlock and the second interlock are unlocked when the drive assembly is in the reset mode, such that proximal movement of the piston rod to the start position is allowed.

According to at least one aspect, for switching the resettable drive assembly from the drive mode to the reset mode, the piston rod is rotatable with respect to the drive member for unlocking the first interlock. According to at least one aspect, for switching the drive assembly from the drive mode to the reset mode, the piston rod and the stop member are rotatable with respect to each other for unlocking the second interlock. For example, the piston rod and the stop member are rotatable with respect to each other and the piston rod additionally or alternatively is rotatable with respect to the drive member.

According one aspect, the drive assembly is configured such that the first interlock and the second interlock are unlockable by rotation of the piston rod from the first angular position to the second angular position, in particular with respect to the housing, to the stop member and/or to the drive member. This embodiment may be particularly expedient when the drive member and the stop member are rotationally locked with respect to the housing.

According to another aspect, the drive assembly is configured such that the second interlock is unlockable by rotation of the stop member in the first rotational direction with respect to the housing and the piston rod. According to at least one aspect, when the second interlock is unlocked, the stop member is operable to interact with the piston rod such that the piston rod follows further rotational movement of the stop member in the first rotational direction with respect to the housing and the drive member for unlocking the first interlock. For example, the piston rod has an axially extending or at least substantially axially extending protrusion—for example the first and/or the second protrusion as described in connection with the piston rod above—which is operable to limit the angular range of motion of the stop member in the first rotational direction with respect to the piston rod.

According to at least one aspect, the resilient member is configured for interacting with the stop member to generate a resilient bias on the stop member for promoting rotation of the stop member in the second rotational direction with respect to the housing, when the drive assembly is in the drive mode. The resilient member may alternatively or additionally be configured for interacting with the stop member to generate a resilient bias on the stop member for promoting rotation of the stop member in the first rotational direction with respect to the housing for unlocking the second interlock and/or the first interlock, when switching the drive assembly from the drive mode to the reset mode.

According to at least one aspect, the stop member has a first part which is axially locked with respect to the housing and a second part which is axially displaceable with respect to the housing. The first and second parts of the stop member may be rotationally coupled, in particular rotationally locked with respect to each other. The second part may be resiliently biased in a first axial direction, for example in the distal direction. The second part may be resiliently biased by means of the resilient member.

According to at least one aspect, either the reset member, the detachable member or the housing is configured for interaction with the second part to convert axial movement of the second part in the first axial direction into rotational movement of the stop member in the second rotational direction, when the drive assembly is in the drive mode. For example, when the drive assembly is in the drive mode, the first diverter element is operable to interact with the second part to deflect the second part in the second rotational direction when the second part moves in the first axial direction. In particular, the second part may bear on the first ramp, which first ramp may be comprised by the reset member, the detachable member or the housing, when the drive assembly is in the drive mode.

According to at least one aspect, either the reset member, the detachable member or the housing interacts with the second part to convert axial movement of the second part in the first axial direction into rotational movement of the stop member in the first rotational direction, i.e. in particular opposite to the second rotational direction, when switching the drive assembly from the drive mode to the reset mode. For example, when switching the drive assembly from the drive mode to the reset mode, the second diverter element is operable to interact with the second part to deflect the second part in the first rotational direction when the second part moves in the first axial direction. In particular, the second part may bear on the second ramp, which second ramp may be comprised of the reset member, the detachable member or the housing, when the drive assembly is switched from the drive mode to the reset mode.

According to at least one aspect, the reset member is releasably engageable with the housing and is operable to retain the drive assembly in the reset mode when it is engaged with the housing. According to at least one aspect, the resilient member is operable to interact with the reset member for locking the reset member in engagement with the housing when the drive assembly is in the reset mode. For example, the resilient member may be operable to generate a resilient bias, in particular in an axial direction, on the reset member.

According to at least one aspect, the detachable member is operable to interact with the reset member such that, when connecting the detachable member to the housing, the reset member is disengaged from the housing. The engagement of the reset member with the housing may be released in particular against the resilient bias on the reset member. According to at least one aspect, when disconnecting the detachable member from the housing, the reset member is brought into engagement with the housing, in particular by means of the resilient bias on the reset member.

According to at least one aspect, the resilient member is a spring which is used for storing energy for driving a rotation of the piston rod in the second rotational direction with respect to the housing during setting of the dose. The energy for driving the rotation in the second rotational direction may be provided by interaction of the spring with the piston rod for biasing the piston rod in the second rotational direction during setting of the dose.

According to at least one aspect, the spring is used for storing energy for driving an axial displacement, in particular an axial displacement of the piston rod, in the proximal direction for reducing pressure of the piston rod on the piston after dispensing of the dose. For example, the spring is used in the drug delivery device, the drug delivery device in particular comprising a cartridge and a piston, the piston being retained within the cartridge and the piston rod being configured for distally displacing the piston with respect to the cartridge for dispensing a dose.

The energy for driving the axial displacement is in particular provided by interaction of the spring with the piston rod for biasing the piston rod in an axial direction, preferably the proximal direction, after dispensing of the dose. It is also conceivable that energy for driving the axial displacement is provided by interaction of the spring with the piston rod for rotationally biasing the piston rod and the drive assembly is operable to convert a rotational movement of the piston rod, driven by the rotational bias, into an axial movement of the piston rod.

According to at least one aspect, the spring is used for interacting with the stop member and/or with the rotational bias member for resiliently biasing the stop member/rotational bias member in the second rotational direction. In one embodiment, when the second interlock is locked, the spring is used for storing energy for driving a rotation of the stop member/rotational bias member in the second rotational direction. For providing the energy, the spring may be configured for interacting with the stop member/rotational bias member for biasing the stop member/rotational bias member in the second rotational direction, when the second interlock is locked.

According to at least one aspect, when unlocking the first and/or second interlocks, the spring is used for transferring force to the stop member for driving a rotation of the stop member in the first rotational direction with respect to the housing and the piston rod by interacting with the stop member for biasing the stop member in the first rotational direction. In one embodiment, the spring is used for storing energy for driving the rotation of the stop member in the first rotational direction. In another embodiment, one end of the spring is coupled to the stop member and another end of the spring is coupled to the reset member. The spring may, for example, be operable to transfer force from the reset member to the stop member, such that, for example, the stop member follows the reset member when the reset member is rotated in the first rotational direction for unlocking the first and/or second interlocks.

According to at least one aspect, the spring is used for resiliently biasing the cartridge in an axial direction when the drug delivery device is in the drive mode for axially and/or rotationally securing the cartridge within the cartridge holder.

According to at least one aspect, the spring is used for resiliently biasing the reset member in an axial direction for locking the reset member in engagement with the housing for retaining the drive assembly in the reset mode.

According to at least one aspect, a piston rod for a drug delivery device is provided for. The piston rod has a proximal end, a distal end and a main longitudinal axis extending between the proximal end and the distal end. The piston rod comprises at least one first ratchet pocket. The first ratchet pocket is axially delimited by a proximal sidewall and a distal sidewall such that the first ratchet pocket tapers in a first angular direction with respect to the axis.

According to at least one aspect, a drive assembly for a drug delivery device is provided for. The drive assembly comprises a housing having a proximal end and a distal end. It comprises a piston rod being axially displaceable and rotatable with respect to the housing between a first angular position and a second angular position. It comprises an axially displaceable drive member and a rotational bias member, which rotational bias member is operable to transfer a resilient bias to the piston rod.

The drive assembly is configured such that, for setting a dose:
 the drive member is proximally axially displaceable with respect to the housing and the piston rod from a rest position to a dose set position;
 when setting the dose, the piston rod is rotated in a first rotational direction and, subsequent to the rotation in the first rotational direction, is rotated in a second rotational direction with respect to the housing and the drive member;
 the drive member interacts with the piston rod to convert proximal axial movement of the drive member with respect to the housing into rotational movement of the piston rod in the first rotational direction towards the second angular position against the resilient bias; and
 the rotational bias member interacts with the piston rod such that the piston rod is rotated in the second rotational direction towards the first angular position with respect to the drive member and the housing by means of the resilient bias.

In this way, a particularly reliably working drive mechanism is achievable.

According to at least one aspect, a resettable drive assembly for a drug delivery device is provided for. The resettable drive assembly comprises a housing having a proximal end and a distal end. The drive assembly comprises a piston rod being rotatable with respect to the housing and being axially displaceable with respect to the housing between a proximal start position and a distal end position. The drive assembly comprises a drive member for distally displacing the piston rod towards the end position when dispensing a dose. The drive assembly further comprises a stop member.

The resettable drive assembly is configured such that:
 the drive member is operable to interact with the piston rod for forming an unlockable first interlock, the first interlock being operable to block proximal movement of the piston rod with respect to the drive member;
 the stop member is operable to interact with the piston rod for forming an unlockable second interlock, the second interlock being operable to block proximal movement of the piston rod with respect to the housing;
 when the drive assembly is in a drive mode, the first and second interlocks are locked such that proximal movement of the piston rod from the end position to the start position is prevented by the first interlock and the second interlock;
 for switching the drive assembly from the drive mode to a reset mode, the piston rod is rotatable with respect to the drive member for unlocking the first interlock, and the piston rod and the stop member are rotatable with respect to each other for unlocking the second interlock; and
 when the drive assembly is in the reset mode, the first interlock and the second interlock are unlocked such that proximal movement of the piston rod to the start position is allowed.

In this way, a particularly reliably working reset mechanism is achievable.

According to at least one aspect, a spring is used in a drug delivery device, the drug delivery device comprising a housing having a proximal end and a distal end, a cartridge, a piston being retained within the cartridge, a piston rod for distally displacing the piston with respect to the cartridge for dispensing a dose, and a drive member for rotating the piston rod in a first rotational direction with respect to the housing when setting the dose. The spring is used for storing energy for driving a rotation of a piston rod in a second rotational direction with respect to the housing by interacting with the piston rod for biasing the piston rod in the second rotational direction during setting of the dose. The spring is additionally used for storing energy for driving an axial displacement for reducing pressure of the piston rod on the piston by interacting with the piston rod for biasing the piston rod in an axial direction after dispensing of the dose.

In this way, a drug delivery device having a particularly low number of resilient parts is achievable.

According to at least one aspect, the spring is used in a resettable drug delivery device, the drug delivery device comprising a housing having a proximal end and a distal end, a piston rod, a drive member for rotating the piston rod in a first rotational direction with respect to the housing when setting a dose and for distally displacing the piston rod away from a proximal start position when dispensing the dose, and a stop member for interacting with the piston rod to form an unlockable interlock. The spring is used for storing energy for driving a rotation of the piston rod in a second rotational direction, opposite to the first rotational direction, with respect to the housing by interacting with the piston rod for biasing the piston rod in the second rotational direction when setting the dose. The spring is additionally used for storing energy for driving a rotation of the stop member in the second rotational direction by interacting with the stop member for biasing the stop member in the second rotational direction when the interlock is locked. The spring is further used for transferring force to the stop member for driving a rotation of the stop member in the first rotational direction with respect to the housing and the piston rod by interacting with the stop member for biasing the stop member in the first rotational direction when unlocking the interlock.

In this way, a resettable drug delivery device having a particularly low number of resilient parts is achievable.

The term "drug delivery device" shall preferably denote a single dose or a multi-dose or a preset dose or a pre-defined, disposable or reusable device, which is designed to dispense a user-selectable or pre-defined dose, i.e. a fixed dose, of a medicinal product. Preferably, it is operable to dispense multiple pre-defined doses, e.g. insulin, growth hormones, low molecular weight heparins, and their analogues and/or derivatives, etc. The device may be of any shape, e.g. compact or pen-type. Dose delivery may be provided through a mechanical (optionally manual) or electrical drive mechanism or a stored energy drive mechanism, the energy, for example, being stored by a spring, etc. The drive mechanism may, for example, comprise the drive assembly. Additionally, the device may contain components designed to monitor physiological properties such as blood glucose levels, etc. Furthermore, the device may comprise a needle or may be needle-free. In particular, the term "drug delivery device" preferably denotes a disposable needle-based pen-type device providing multiple pre-defined doses having mechanical and manual dose delivery and dose selection mechanisms. The device is preferably designed for use by persons without formal medical training, such as patients. Preferably, the drug delivery device is of the injector type.

The term "housing" shall preferably denote an exterior housing, sometimes also denoted as "main housing", "body", or "shell", and/or an interior housing, sometimes also denotes as "insert" or "inner body". The housing may have a unidirectional axial coupling to prevent proximal movement of specific components. It may be designed to enable the safe, correct and comfortable handling of the assembly, the drug delivery device or any of its mechanism(s). Usually, it is designed to house, fix, protect, guide and/or engage with any of the inner components of the drive assembly and/or the drug delivery device, for example with the drive assembly, a cartridge, a piston, and/or the piston rod. It may be designed for limiting the exposure of the inner components to contaminants, such as liquid, dust, dirt, etc. In general, the housing may be unitary or a multi-part component. It may have a tubular or non-tubular shape. Usually, an exterior housing serves to house a cartridge from which a number of doses of a medicinal product may be dispensed. According to at least one aspect, the exterior housing is provided with a plurality of last-dose-stops adapted to be abutted by an axial stop provided on the drive member.

The term "drive member" preferably denotes a component being adapted to operate through/within the housing. It may be designed to translate axial movement through/within the drive assembly or the drug delivery device, respectively. For example, it translates axial movement from an actuation component, such as a push button, to the piston rod. In a preferred embodiment, the drive member is further releasably engaged with the piston rod, for example by means of the first interlock. The term "releasably engaged" shall preferably mean that two components of the assembly or device are joined for translation of force or movement in one direction only, preferably during dispense. The drive member may be of unitary or multi-part construction.

The term "piston rod" preferably denotes a component adapted to operate through/within the housing body, designed to translate axial movement through/within the assembly or the device, respectively. Preferably, it translates axial movement from the drive member to the piston, e.g. for the purpose of discharging, dispensing an injectable product such as a liquid medicinal product.

The "distal end" of the assembly, the device or a component of the device or of the assembly—for example of the housing and/or the piston rod—, shall preferably denote that end, which is to be disposed closest or which is disposed closest to the dispensing end of the device. The "proximal end" of the assembly, the device or a component of the device or of the assembly shall preferably denote that end, which is to be disposed furthest away or which is furthest away from the dispensing end of the device.

The term "drug" or "medicinal product", as used herein, preferably means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exedin-3 or exedin-4 or an analogue or derivative of exedin-3 or exedin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin;

B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exedin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

Features described in connection with different aspects may be combined with one another and also combined with further features described below.

The disclosure content of the claims is explicitly incorporated into the description by reference.

Advantageous embodiments and developments of the piston rod, the drive assembly, the drug delivery device, and the use of the spring will become apparent from the exemplary embodiments described below in association with the figures.

BRIEF DESCRIPTION OF THE FIGURES

FIG. 1B shows a sectional view of the drive assembly according to the first exemplary embodiment in a first drive mode configuration, e.g. a dose set configuration, FIG. 1C shows a sectional view of the drive assembly according to the first exemplary embodiment, in a second drive mode configuration, e.g. a dose dispensed configuration, FIG. 2A shows a sectional view of the drive assembly according to the first exemplary embodiment in a fully dispensed configuration, FIG. 2B shows a sectional view of the drive assembly according to the first exemplary embodiment in a first reset mode configuration, FIG. 2C shows a sectional view of the drive assembly according to the first exemplary embodiment in a second reset mode configuration, FIG. 5A shows a partial side view of the drive assembly according to the second exemplary embodiment in a third drive mode configuration, e.g. a configuration during dispensing the set dose, FIG. 5B shows a partial side view of the drive assembly according to the second exemplary embodiment in a fourth drive mode configuration, e.g. a dose dispensed configuration, FIG. 6A shows a partial side view of the drive assembly according to the second exemplary embodiment in a configuration during switching the assembly from the drive mode to the reset mode, FIG. 6B shows a partial side view of the drive assembly according to the second exemplary embodiment in the reset mode, FIG. 7 shows a sectional side view of a drive assembly according to a variant of the second embodiment, FIG. 10A shows a side view of the piston rod of the drive assembly according to the second embodiment, FIG. 10B shows a side view of a variant of the piston rod of FIG. 10A.

In the exemplary embodiments and figures, similar or similarly acting constituent parts are provided with the same reference symbols.

DETAILED DESCRIPTION

Figure 1A:
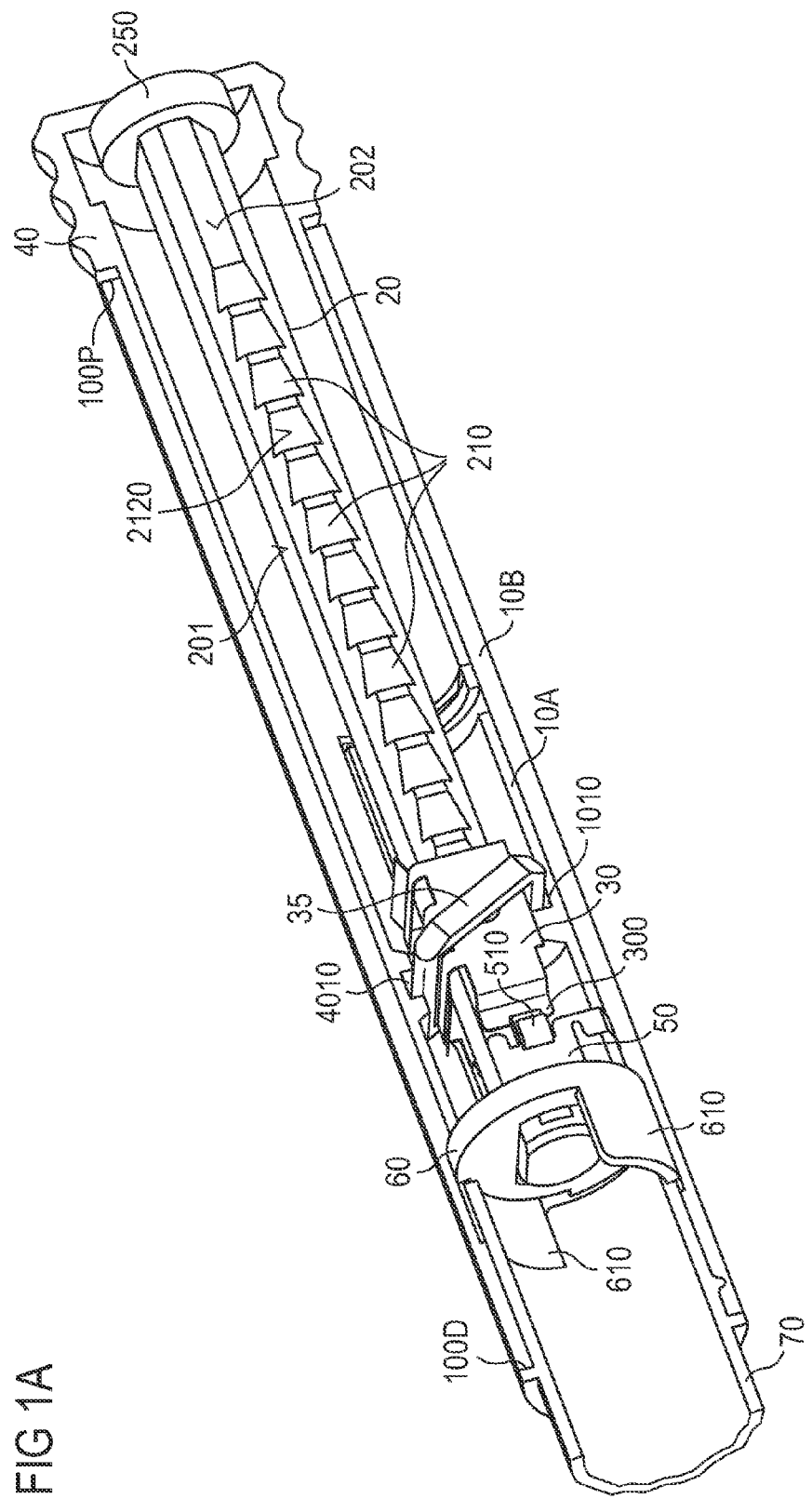
FIG. 1A shows an oblique sectional view of a drive assembly according to a first exemplary embodiment in a start configuration.

FIG. 1A shows an oblique sectional view of a drive assembly according to a first exemplary embodiment. In the first embodiment, the drive assembly may be a resettable drive assembly. The resettable drive assembly may have a drive mode and a reset mode.

The drive assembly has a housing 10A, 10B. For example, the housing comprises an exterior housing 10B and a pivot part 10A. It is also conceivable that the housing is of unitary construction. The housing 10A, 10B has a proximal end 100P and a distal end 100D. The pivot part 10A is preferably fixed with respect to the exterior housing 10B, in particular it is locked with respect to axial and/or rotational movement against the exterior housing 10B.

The drive assembly further comprises a piston rod 20. The piston rod has a longitudinal axis running in the direction from the proximal end 100P of the housing 10A, 10B to the distal end 100D. The piston rod 20 may have a last-dose-stop element 250 at its proximal end. The last-dose-stop element 250 may be formed as an outwardly directed shoulder or flange at the proximal end of the piston rod 20.

The piston rod may have a non-circular cross-section. For example, it has a flat side surface 201. In the present embodiment, the piston rod 20 has two opposite flat side surfaces 201. The two flat side surfaces 201 are in particular parallel or at least substantially parallel with respect to each other. The two flat side surfaces are arranged such that the longitudinal axis extends between the two flat side surfaces 201.

At least one further side surface 202 of the piston rod—two opposing further side surfaces 202 of the piston rod 20 in the present embodiment—may be provided with a row of ratchet pockets 210. The row is oriented axially. Each ratchet pocket 210 is bound by a proximal surface 2120 and a distal surface 2110 such that the ratchet pocket 210 tapers in a radial direction towards the longitudinal axis of the piston rod 20. The proximal surface 2120 may have a distal edge and an opposite, proximal edge. The distal edge may be arranged at a shorter distance from the longitudinal axis than the proximal edge. The distal surfaces 2110 of the ratchet pockets 210 extend, for example, perpendicular or substantially perpendicular to the longitudinal axis. The ratchet pockets 210 may have an undercut which may be formed by the respective distal surfaces 2110, for example. For example, the distal surface 2110 may have a distal edge and an opposite, proximal edge. The distal edge may be arranged at a shorter distance from the longitudinal axis than the proximal edge.

The further side surface(s) 202, which is/are provided with the row of ratchet pockets 210, may be curved or comprise at least one respective beveled or curved longitudinal edge region, which edge region is in particular connected to one of the flat side surfaces 201.

The drive assembly further has a drive member 30. The drive member 30 may be axially displaceable with respect to the housing 10A, 10B, the range of axial motion of the drive member 30 preferably being limited by interaction with the housing 10A, 10B. The drive member 30 may be rotationally locked with respect to the housing 10A, 10B. The drive member 30 may be designed as a drive sleeve or a carrier plate in the present embodiment, the piston rod 20 may extend through the drive member 30.

The drive member may be operable to interact with the piston rod 20 for forming a first interlock. The first interlock may be operable to block proximal movement of the piston rod 20 with respect to the drive member 30. For example, the drive member 30 may comprise a pawl element 300. The pawl element 300 may be designed in form of a lug protruding from the drive member 30, for example in the distal direction—as in the present embodiment—or the proximal direction. The pawl element 300 may be configured for interacting with the ratchet pockets 210 of the piston rod 20. The pawl element is expediently resilient such that it is radially displaceable with respect to the longitudinal axis.

The drive assembly comprises a push button 40. The push button 40 may at least partially extend between the housing, in particular the exterior housing 10B, and the piston rod and/or between the housing, in particular the exterior housing 10B, and the drive member 30. The push button 40 may be configured for interacting with the drive member 30, in particular for axially displacing the drive member 30. The push button 40 may comprise, for example, an actuation sleeve which at least partially surrounds the piston rod 20 and/or the drive member 30.

The drive assembly may also comprise a lever 35. One side of the lever 35 may be retained in a fixed pivot 1010. The fixed pivot is in particular axially and rotationally fixed with respect to the housing 10A, 10B. The fixed pivot 1010 may be comprised by the pivot part 10A of the housing. Another, preferably opposite, side of the lever 35 may be retained in a moving pivot 4010 which moving pivot 4010 may be comprised by the push button 40. The moving pivot 4010, and in particular the push button 40, may be axially displaceable with respect to the housing 10A, 10B and, preferably, rotationally locked with respect to the housing 10A, 10B. The drive member 30 may be rotationally locked with respect to the housing 10A, 10B by means of interaction with the housing 10A, 10B via the lever 35 and the fixed pivot 1010 and/or the moving pivot 4010.

The lever 35, for example, interacts with the fixed pivot 1010 and the moving pivot 4010 by means of a respective axle which may engage a slot of the respective pivot 1010, 4010. In the present embodiment, the lever 35 has one axle which is retained in a slot of the fixed pivot 1010 and a further axle being retained in a slot of the moving pivot 4010. The two axles may, for example, be connected to each other by means of two lever arms, such that the lever arms and the axles together form a closed ring-like element which may have a rectangular shape, for example. The piston rod 20 may run through the lever 35. For example, the piston rod is completely laterally surrounded by the lever 35.

The lever 35 may comprise journal bearings for interacting with the drive member 30. For example, the journal bearings are arranged on a central axis of the lever 35. The central axis is, for example, parallel to the axles. In the present embodiment, the central axis bisects the lever arms. The journal bearings may, for example, extend into respective holes of the drive member 30. The drive member may be axially locked with respect to the journal bearings of the lever 35.

The drive assembly further comprises a stop member 50. The stop member 50 may be locked with respect to axial and rotational movement with respect to the housing 10A, 10B.

The stop member 50 may be operable to interact with the piston rod 20 for forming a second interlock. The second interlock may be operable to block proximal movement of the piston rod 20 with respect to the housing 10A, 10B. Expediently, the stop member 50 comprises a pawl element (not explicitly shown in FIG. 1A) for interacting with the ratchet pockets 210 of the piston rod 20. In the present embodiment, the stop member 50 and the drive member 30 interact with the same row(s) of ratchet pockets 210.

The stop member 50 may comprise a suspension element 510 for connecting the stop member 50 to the housing. The suspension element 510 may, in particular, be operable for resiliently biasing the pawl element of the stop member 50 in a radial direction with respect to the longitudinal axis. The suspension element 510 may, for example, have an S-shaped bend.

The first and second interlocks may be unlockable. The first and second interlocks may be locked when the drive assembly is in the drive mode and unlocked when the drive assembly is in the reset mode. When the first (second) interlock is locked, the pawl element 300 of the drive member 30 (the stop member 50) may disengage from one ratchet pocket 210 of the piston rod 20 by an radial movement of the respective pawl element with respect to the longitudinal axis of the piston rod when the piston rod 20 is axially moving with respect to the drive member 30 (stop member 50). When switching the drive assembly from the drive mode to the reset mode, the pawl element 300 of the drive member 30 (stop member 50) may be brought out of engagement from the respective ratchet pocket 210 of the piston rod 20 by a rotation of the piston rod with respect to the drive member 30 (stop member 50).

The drive assembly may further comprise a reset member 60. The reset member 60 may be axially locked with respect to the housing 10A, 10B. The reset member 60 may preferably be rotatable with respect to the housing 10A, 10B for switching the drive assembly from the drive mode to the reset mode. The drive assembly may be configured for unlocking the first and/or second interlock by means of a rotational movement of the reset member 60 around the longitudinal axis with respect to the housing 10A, 10B.

The reset member 60 may comprise, for example, a ring-like part with an opening through which the piston rod 20 may extend. The form of the opening may be selected such that the piston rod 20 is splined to the reset member 60. In particular, the piston rod and the opening are designed such that the piston rod, when extending through the opening, is rotationally locked and axially displaceable with respect to the reset member 60. For example, the opening has at least one flat which is operable to interact with a respective flat side surface 201 of the piston rod 20 for rotationally locking the piston rod 20 with respect to the reset member 60.

According to one aspect, the reset member 60 has tooth elements 610 provided for interacting with a detachable member 70. The tooth elements 610 may distally protrude from the reset member 60, for example. The detachable member 70 may, for example, be one of a cartridge and a cartridge holder. The cartridge holder may be designed to retain a cartridge. In particular, the detachable member 70 has indentations for engagement with the tooth elements 610. Expediently, the drive assembly may be configured such that a spline connection between the detachable member 70 and the reset member 60 is formed when the tooth elements 610 engage the indentations.

The drive assembly, in particular the detachable member 70 and the housing 10A, 10B, may be configured such that detaching the detachable member 70 from the housing 10A, 10B involves rotating the detachable member 70 with respect to the housing 10A, 10B. For example, the detachable member 70 and the housing 10A, 10B may be designed such that a bayonet connection or a thread connection can be established between the detachable member 70 and the housing. The drive assembly may be configured such that the reset member 60 follows rotational movement of the detachable member 70 with respect to the housing 10A, 10B for detaching the detachable member 70 from the housing 10A, 10B by means of interaction between the tooth elements 610 of the reset member 60 and respective indentations of the detachable member 70. The detachable member 70 may be rotationally locked and axially displaceable with respect to the reset member 60 when the tooth elements 610 of the reset member 60 are in engagement with the respective indentations of the detachable member 70. The drive assembly may be configured such that the tooth elements 60 are disengageable from the indentations by means of a distal displacement of the detachable member 70 with respect to the housing 10A, 10B and the reset member 60 for unlocking the thread or bayonet connection.

In FIG. 1A, the drive assembly is in the drive mode. In particular, it is in a start configuration. In the start configuration, the drive assembly may be ready for setting a dose, in particular a first dose. The piston rod 20 may be in a proximal start position with respect to the housing 10A, 10B when the drive assembly is in the start configuration. In the proximal start position, the piston rod 20 may be arranged in an axial position which is closest to the proximal end 100P of the housing 10A, 10B.

When operating the drive assembly, in particular for setting a dose—for example a dose of a liquid medicinal product—, the push button 40 is proximally displaced with respect to the housing 10A, 10B. By means of displacing the push button 40 in the proximal direction, the moving pivot 4010, which is comprised by or connected to the push button 40, is proximally displaced with respect to the fixed pivot 1010.

That axle of the lever 35 which is retained in the slot of the moving pivot 4010 is carried in the proximal direction with the moving pivot 4010, such that the lever 35 is rotated around its engagement with the fixed pivot 1010. In this way, axial movement of the push button 40 is transformed into a rotation of the lever 35 around its axle retained in the fixed pivot 1010.

The rotation of the lever 35 is, in turn, converted into axial movement of the drive member 30 by means of the drive member interacting with the journal bearings of the lever 35. A mechanical advantage is achieved by means of the lever 35 such that the drive member 30 is displaced by a smaller distance in the proximal direction than the push button 40. In particular, the central axis of the lever 35, which is connected to the drive member 30, and the axle of the lever 35 which is retained in the moving pivot 4010 are rotated by the same angle around the fixed pivot 1010. However, since said axle is arranged at a larger distance from the fixed pivot 1010 than the central axis, for example twice the distance, the distal displacement of the push button 40 is larger than, for example twice, the distal displacement of the drive member 30.

When the drive member 30 is proximally displaced with respect to the housing 10A, 10B, the pawl element 300 of the drive member 30 disengages from one ratchet pocket 210 and subsequently engages the proximally successive ratchet pocket 210 of the piston rod 20. During its movement from one ratchet pocket 210 to the next ratchet pocket 210, the pawl element 300 of the drive member 30 bears on and is displaced along the proximal sidewall of the previous ratchet pocket 210. Since the proximal sidewall is inclined such that a proximal end of the proximal sidewall has a larger distance from the longitudinal axis of the piston rod 20 than a distal end of the proximal sidewall, the pawl element 300 is displaced away from the longitudinal axis in a radial direction during movement of the drive member 30 from one ratchet pocket to the proximally successive ratchet pocket 210. The drive member is designed such that the radial displacement generates a resilient bias on the pawl element 300. By means of the resilient bias, engagement of the pawl element 300 of the drive member 30 with the next ratchet pocket 210 is promoted. Engagement with and/or disengagement from the ratchet pockets 210 may be audible and/or palpable for a user setting the dose. Thus, the user may be provided with audible and/or tactile feedback for the dose-set operation.

During proximal movement of the drive member 30, proximal movement of the piston rod 20 is blocked by means of the second interlock, formed by the stop member 50 and the piston rod 20. In particular, the pawl element of the stop member 50 remains in engagement with one of the ratchet pockets 210 during proximal movement of the drive member 30 for setting the dose. In this way, axial load in the proximal direction exerted on the piston rod 20 due to interaction with the drive member 30 when the drive member 30 is proximally displaced with respect to the piston rod 20 for setting the dose is countered by means of the second interlock, so that the piston rod 20 preferably does not follow the proximal movement of the drive member 30. Thus, the dose accuracy may be advantageously increased.

FIG. 1B shows a sectional view of the drive assembly in a first drive mode configuration, e.g. a dose set configuration, after proximal displacement of the push button 40 for setting the dose was completed.

In the dose set configuration, the drive member 30 and the push button 40 are proximally displaced with respect to the piston rod 20 and the housing 10A, 10B compared to the start configuration of FIG. 1A. Due to interaction with the stop member 50, the piston rod is in the same position with respect to the housing 10A, 10B as in the start configuration.

FIG. 1C shows a sectional view of the drive assembly in a second drive mode configuration, e.g. the dose dispensed configuration. For example, for dispensing the set dose, the drive assembly may be brought from the dose set configuration of FIG. 1B to the dose dispensed configuration of FIG. 1C.

For dispensing the set dose, the push button 40 may be distally displaced with respect to the housing 10A, 10B. Distal movement of the push button 40 is converted into a rotation of the lever 35 around the fixed pivot 1010. During dispensing the dose, the lever 35 rotates in the opposite direction compared to its rotation for setting the dose. In particular, the axle of the lever 35 which is retained in the slot of the moving pivot 4010 is distally displaced with respect to the housing 10A, 10B during dispensing the set dose. The rotation of the lever 35 is in turn converted to distal axial movement of the drive member 30 by means of interaction of the drive member 30 with the lever 35 via the journal bearings.

During the distal movement of the drive member 30 the first interlock blocks proximal movement of the piston rod 20 with respect to the drive member 30, such that the drive member 30 carries the piston rod 20 with it in the distal direction. In particular, the pawl element 300 of the drive member 30 remains engaged with one ratchet pocket 210 of the piston rod 20 when the drive member 30 is distally displaced for dispensing the set dose. The pawl element 300 preferably abuts the distal surface of the ratchet pocket 210. The piston rod 20 may be operable to distally displace a piston of the cartridge for dispensing the set dose from the cartridge.

The second interlock is configured to allow distal displacement of the piston rod 20 with respect to the housing. Thus, when the piston rod 20 moves in the distal direction, the pawl element of the stop member 50 disengages from one ratchet pocket 210 and engages with a proximally subsequent ratchet pocket 210 of the piston rod 20. When disengaging from the ratchet pocket, pawl element 500 of stop member 50 may be radially outwardly displaced, in particular against the resilient bias of the suspension element 510. The resilient bias generated by the suspension element 510 may promote engagement with the subsequent ratchet pocket 210. Engagement with and/or disengagement from the ratchet pockets 210 may be audible and/or palpable for the user dispensing the dose. Thus, the user may be provided with audible and/or tactile feedback for the dose-dispense operation.

The drive assembly may be operable for dispensing a plurality of doses. The doses may be fixed doses, i.e. pre-set and non-user variable doses. The volume of one dose may be determined by the distance between the distal surfaces 2110 of two directly subsequent ratchet pockets 210, for example.

The piston rod may be movable from the proximal start position to a distal end position, for example by repeating dose-set and dose-dispense operations as described in connection with FIGS. 1A to 1C, until the drive assembly is in a fully-dispensed configuration.

FIG. 2A shows a sectional view of the drive assembly according to the first embodiment in the fully dispensed configuration. In the fully dispensed configuration, when the piston rod 20 is in the distal end position, the piston rod 20, in particular the last-dose-stop element 250 of the piston rod 20, interacts with the housing 10A, 10B so that further distal movement of the piston rod 20 is prevented. In particular, the piston rod 20 cannot be removed from the drive assembly by being pulled in the distal direction.

For preventing further distal movement, the piston rod 20 can either interact directly with the housing 10A, 10B or via further components of the drive assembly such as the drive member 30, the lever 35 and/or the push button 40. In the present embodiment, when the drive assembly is in the fully dispensed configuration, the drive member 30 is configured to interact with the housing 10A, 10B—for example via the lever 35 and the push button 40—, such that distal movement of the drive member 30 with respect to the housing 10A, 10B is blocked. In addition, the last-dose-stop element 250 abuts a proximal end of the drive member 30 when the drive assembly is in the fully dispensed configuration, such that distal movement of the piston 20 with respect to the drive member 30, and in turn with the housing 10A, 10B, is blocked.

The last-dose-stop element 250 of the piston rod 20 blocks proximal movement of the drive member 30 with respect to the piston rod. Proximal movement of the piston rod 20 with respect to the housing from the distal end position back towards the proximal start position is prevented by the second interlock also in the fully dispensed configuration—in particular by engagement of the pawl element of the stop member 50 with one ratchet pocket 210 of the piston rod 20. In this way, proximal movement of the drive member 30 is blocked when the drive assembly is in the fully dispensed configuration. Since the push button 40 is coupled to the drive member 30 by means of the lever 35, proximal movement of the push button 40 with respect to the housing 10A, 10B is also blocked in the fully dispensed configuration. In this way, the drive assembly is inoperable for setting a further dose in the fully dispensed configuration.

For resetting the drive assembly from the fully dispensed configuration of FIG. 2A to the start configuration of FIG. 1A, the drive assembly may be switched from the drive mode to the reset mode. For switching from the drive mode to the reset mode, reset member 60 may be rotated with respect to the housing 10A, 10B around the longitudinal axis of the piston rod 20 and the housing 10A, 10B.

For example, the drive assembly is switched from the drive mode when detaching the detachable member 70 from the housing 10A, 10B, in particular by disconnecting the bayonet connection or thread connection which may be formed between the detachable member 70 and the housing 10A, 10B. Disconnecting the detachable member 70 from the housing 10A, 10B may preferably comprise rotating the detachable member 70 with respect to the housing 10A, 10B around the longitudinal axis of the piston rod 20 and the housing 10A, 10B. The rotational movement of the detachable member 70 may be transferred to rotational movement of the reset member 60 by means of interaction between the tooth elements 610 of the reset member 60 and respective indentations of the detachable member 70. When the drive assembly is in the reset mode, the indentations of the detachable member 70 may be disengaged from the tooth elements 610 such that further rotation of the detachable member 70—for example for completely detaching the detachable member 70 from the housing 10A, 10B—is not transferred to the reset member 60. Thus, when the drive assembly is in the reset mode, the detachable member 70 may, for example, be unscrewed from the housing 10A, 10B or pulled in the distal direction for completely disconnecting the detachable member 70 from the housing 10A, 10B.

FIG. 2B shows a sectional view of the drive assembly according to the first embodiment in a first reset mode configuration. In the first reset mode configuration, the detachable member 70 is disconnected from the housing 10A, 10B and the reset member 60 is rotated with respect to the housing 10A, 10B, for example by an angle of 90°, compared to the angular orientation of the reset member 50 with respect to the housing 10A, 10B in the drive mode.

Since the piston rod 20 is splined to the reset member 60, the piston rod 20 follows the rotation of the reset member 60. Therefore, in the reset mode, the piston rod 20 is rotated with respect to the housing 10A, 10B around the longitudinal axis compared to its angular orientation in the drive mode by the same amount as the reset member 60.

The drive member 30 and the stop member 50, however, are rotationally locked with respect to the housing 10A, 10B. In this way, the reset member 60 and the piston rod 20 are rotationally displaced with respect to the drive member 30 and the stop member 50 by means of the rotation of the reset member 60.

By means of rotating the piston rod 20 with respect to the drive member 30 and the stop member 50, the respective row or rows of ratchet pockets 210 is/are rotated out of engagement with the respective pawl elements of the drive member 30 and the stop member 50. After rotation of the reset member 60 and the piston rod 20, the pawl elements of drive member 30 and stop member 50, respectively, bear on a respective flat side surface 201 of the piston rod 20. The ratchet pockets 210—or at least those ratchet pockets 210 which engage the pawl elements of the drive member 30 and the stop member 50 in the fully-dispensed configuration of the drive assembly—may have a breakthrough or an opening at least in one angular direction with respect to the longitudinal axis to facilitate rotation of the pawl elements out of the respective ratchet pocket 210. For example at least one ratchet pocket 210 may not be bound by a side face in at least one angular direction with respect to the longitudinal axis. Rotation of the pawl elements out of the ratchet pockets may alternatively or additionally be facilitated by the curved or beveled shape of the side surface(s) comprising the ratchet pockets 210.

When the pawl elements of the drive member 30 and the stop member 50, respectively, bear on the flat side surface(s) 201 of the piston rod 20, the first and second interlocks are unlocked. Proximal movement of piston rod 20 with respect to the housing is no longer blocked by the unlocked first and second interlocks. Thus, the piston rod 20 can be pushed back to its proximal start position. When being pushed back to the proximal start position, the piston rod may advantageously be only axially displaced. No rotation of the piston rod is necessary.

FIG. 2C shows a schematic sectional view of the drive assembly in a second reset mode configuration after the piston rod 20 has been pushed back to its proximal start position.

For switching the drive assembly from the reset mode to the drive mode, reset member 60 is rotated with respect to the housing 10A, 10B. For example, the reset member 60 is rotated in the opposite direction as for switching from the drive mode to the reset mode. The rotation can, for example, be effected by means of interaction of the tooth elements 610 with the respective indentations of the detachable member 70 during connecting the detachable member 70 to the housing 10A, 10B. The detachable member 70 may preferably be connected to the housing 10A, 10B for providing the drive assembly with a full cartridge. In this way, rotation of the detachable member 70 around the longitudinal axis for connecting the detachable member 70 to the housing 10A, 10B may be transferred to the reset member 60, such that the reset member 60 is rotationally displaced with respect to the housing 10A, 10B.

Rotational movement of the reset member 60 for switching the drive assembly from the reset mode to the drive mode is, in turn, transferred to rotational movement of the piston rod 20 around the longitudinal axis with respect to the housing 10A, 10B, the drive member 30 and the stop member 50. In this way, the pawl elements of the drive member 30 and stop member 50, respectively, are brought into engagement with a respective ratchet pocket 210 of the piston rod 20, so that the first and second interlocks are locked and the drive assembly was reset and is again in the start configuration of FIG. 1A.

Figure 3:
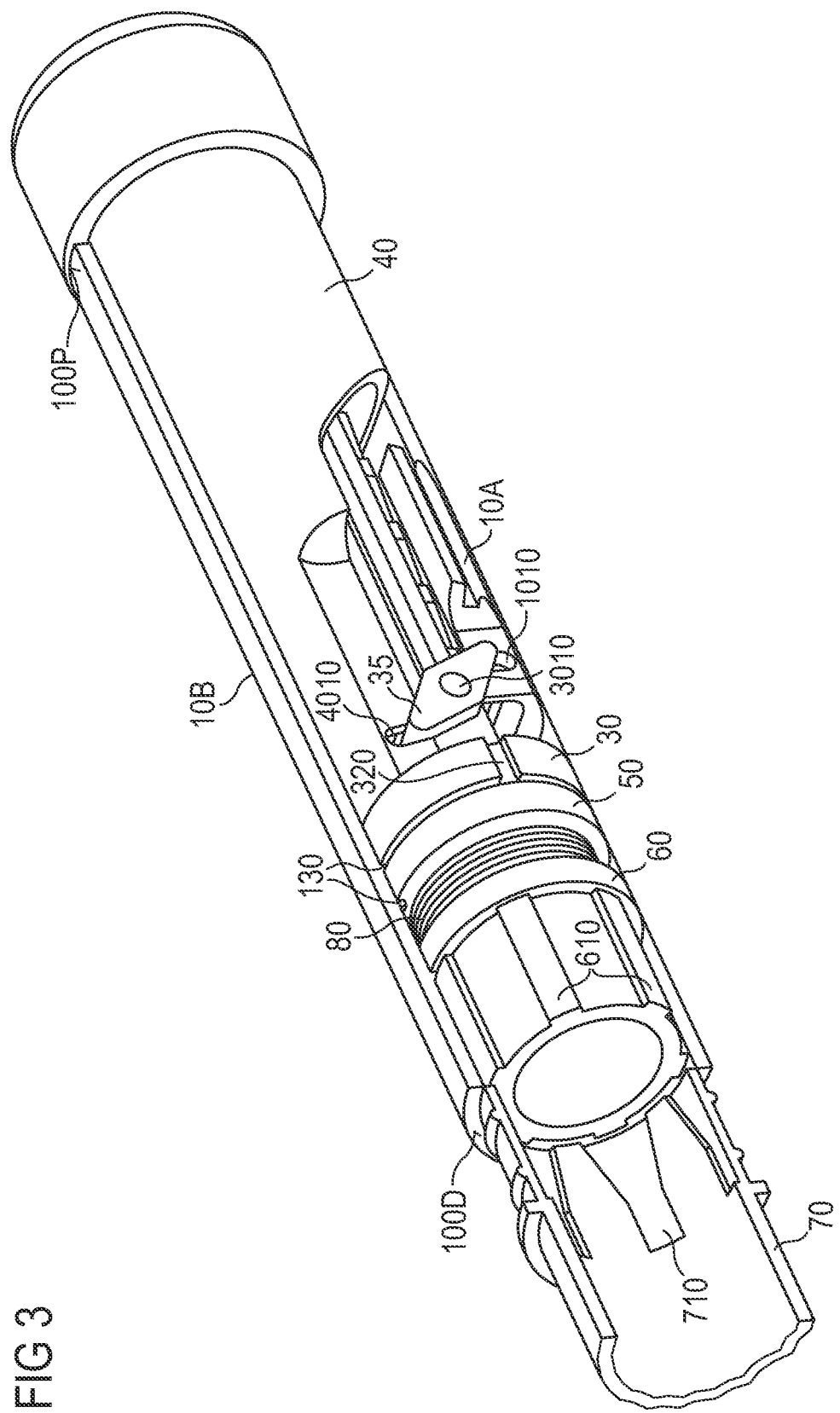
FIG. 3 shows an oblique sectional view of a drive assembly according to a second exemplary embodiment.

FIG. 3 shows an oblique sectional view of a drive assembly according to a second exemplary embodiment.

The drive assembly comprises an exterior housing 10B and a pivot part 10A fixed to the exterior housing. The drive assembly further comprises a push button 40 which is axially displaceable and, preferably, rotationally locked with respect to the housing 10A, 10B.

In addition, the drive assembly comprises a drive member 30. The drive member 30 may be axially displaceable with respect to the housing 10A, 10B. The drive member 30 may be configured to be operatively connected with the push button 40 by means of a lever 35. The lever 35 may, for example, comprise a pair of lever arms. Each lever arm may have a first axle, in particular being arranged at one end of the lever arm, for engaging a slot of a fixed pivot 1010, the fixed pivot 4010 preferably being comprised by the housing, in particular the pivot part 10A of the housing. Each lever arm may have a second axle, in particular being arranged at an opposite end of the lever arm as compared to the first axle, for engaging a slot of a moving pivot 4010, the moving pivot 4010 preferably being comprised by the push button 40. The lever 35 may be rotatable around the engagement of the first axles of the lever arms with the fixed pivot 1010.

The drive member 30 may be connected to the lever 35 by means of journal bearings 3010. For example, each lever arm may comprise a hole or slot for engaging one respective journal bearing 3010 of the drive member 30. In particular, the central axis of lever 35 runs through the journal bearings 3010. A mechanical advantage is realized by means of the arrangement of the moving pivot 4010 and the journal bearings 301 at different distances from the fixed pivot 1010. For example, the drive member 30 may travel half the axial distance travelled by the push button 40, thus providing for a 1:2 mechanical advantage. Other mechanical advantages are conceivable, as well.

In a similar fashion as described in connection with the first exemplary embodiment, axial movement of the push button 40, in particular for setting or dispensing a dose, is converted to rotational movement of the lever 35 around the first axles engaging the slot of the fixed pivot 1010. This rotation is in turn converted into axial movement of the drive member 30 in the same direction as the push button 40.

The drive member 30 may be rotationally locked with respect to the housing 10A, 10B. For example, the drive member 30 has an axially extending groove 320 which is configured for engaging an axially extending web of the housing 10A, 10B for rotationally locking the drive member 30 with respect to the housing 10A, 10B and allowing axial movement of the drive member 30 with respect to the housing 10A, 10B. Accordingly, the drive member 30 may be splined to the housing 10A, 10B. The axial range of motion of the drive member may be limited by interaction with the housing 10A, 10B, for example via the lever 35 and/or the push button 40.

The drive assembly also comprises a stop member 50 which is axially fixed and rotatable with respect to the housing, for example by means of a pair of circumferential protrusions 130, e.g. forming a notch, on an inner surface of the exterior housing 10B, preferably interacting with a circumferential bulge of the stop member 50.

The drive assembly may comprise a reset member 60 which may be rotatable but axially locked with respect to the housing 10A, 10B. The reset member 60 may have tooth elements 610. In contrast to the first embodiment, the tooth elements 610 do not protrude distally from the reset member 60. Rather, the tooth elements 610 protrude radially inwardly from an inner, in particular circumferential, surface of the reset member 60.

The detachable member 70 may have indentations 710, in particular in an inner surface of the detachable member 70, which are configured for engaging with respective tooth elements 610 when the detachable member 70 is connected to the housing 10A, 10B. In FIG. 3, the detachable member 70 is illustrated in a position separated from the housing 10A, 10B to allow the indentations 710 to be viewed.

The drive assembly according to the present embodiment comprises a spring 80 which is operable to interact with the stop member 50 and the reset member 60. For example, the spring 80 is a coil spring with an opening through which the piston rod extends. The spring 80 may be axially positioned between the stop member 50 and the reset member 60. One end of the spring 80 may be axially and rotationally fixed to the stop member and an opposite end of the spring may be axially and rotationally fixed to the reset member 60.

The drive assembly also comprises a piston rod 20. The piston rod 20 may be axially displaceable with respect to the housing 10A, 10B and rotatable with respect to the housing 10A, 10B between a first angular position and a second angular position. The first and second angular positions may be angularly spaced apart by less than 360°, in particular by 90° or less.

FIG. 10A shows a side view of the piston rod 20 for the drive assembly according to the second exemplary embodiment.

The piston rod 20 has a proximal end 200P and a distal end 200D. A main longitudinal axis extends between the proximal end 200P and the distal end 200D. The piston rod may comprise a main body 20A and a bearing 20B which is rotatable with respect to the main body 20A. The main body 20A and the bearing 20B are preferably axially locked with respect to each other. For example, a ball-and-socket joint may be formed between the main body 20A and the bearing 20B.

The piston rod 20 has an axial row of first ratchet pockets 210. Each of the first ratchet pockets 210 is axially bound by a distal sidewall 2110 and a proximal sidewall 2120, such that the first ratchet pocket 210 tapers in a first angular direction with respect to the longitudinal axis. The piston rod 20 may have a ridge with indentations which form the first ratchet pockets 210.

Each of the distal sidewall 2110 and the proximal sidewall 2120 of one of the first ratchet pockets 210 extends in the first angular direction from a first edge to a second edge. The first and second edges may extend radially, in particular perpendicularly, with respect to the longitudinal axis. In the present embodiment, the second edges of the first and second sidewalls 2110, 2120 coincide and define one end of the first ratchet pocket 210. It is also conceivable that the second edges of the first and second sidewalls 2110, 2120 are spaced apart and connected by a further sidewall. The further side wall may extend axially, for example. The first edge of the proximal side wall 2110 of one first ratchet pocket 210 may be connected to the first edge of the distal side wall 2120 of the axially successive first ratchet pocket 210 by a connecting wall 2130 which extends, for example, axially or substantially axially.

The first edge of the proximal side wall 2110 is arranged further away from the distal end 200D of the piston rod 20 than the second edge of the proximal side wall 2110. Thus, the proximal sidewall 2110 may be inclined with respect to the longitudinal axis as seen in plan view onto the first ratchet pocket 210 and the piston rod. The distal side wall 2120 may run essentially perpendicular to the longitudinal axis.

The piston rod 20, in particular the main body 20A of the piston rod, may have a first axially extending protrusion 230. The protrusion 230 forms a channel 240 in cooperation with the axial row of first ratchet pockets 210. The first ratchet pockets 210 represent bulges of the channel 240. For example, the channel 240 is bound in the first angular direction by the first ratchet pockets 210 of the axial row and the connecting walls between axially successive first ratchet pockets 210. The channel 240 may be bound in a second angular direction, opposite to the first angular direction by the first protrusion 230.

The piston rod 20 according to the present embodiment additionally has second ratchet pockets 220 which are also arranged in an axially successive fashion, i.e. the piston rod 20 has an axial row of second ratchet pockets 220. Similar to the first ratchet pockets 210, the second ratchet pockets are axially bound by a distal sidewall 2210 and a proximal sidewall 2220. However, the second ratchet pockets do not taper in the first angular direction. Rather, each second ratchet pocket 220 is axially delimited by the distal sidewall 2210 and the proximal sidewall 2220 such that the second ratchet pocket tapers in the second angular direction, opposite to the first angular direction. The second ratchet pockets 220 may be formed by indentations in the ridge which ridge also comprises the row of first ratchet pockets 210. In particular, the indentations forming the second ratchet pockets 220 may be comprised by a side face of the ridge which side face is opposite of the side face comprising the indentations which form the first ratchet pockets 210.

Each of the distal sidewall 2210 and the proximal sidewall 2220 of the one second ratchet pocket 220 extends in the second angular direction from a first edge to a second edge. The first and second edges may extend radially, in particular perpendicular, with respect to the longitudinal axis. In the present embodiment, the second edges of the first and second sidewalls 2210, 2220 coincide and define one end of the second ratchet pocket 220. It is also conceivable that the second edges of the first and second sidewalls 2210, 2220 are spaced apart and connected by a further sidewall. The further side wall may extend axially, for example. The first edge of the proximal side wall 2210 of one second ratchet pocket 220 may be connected to the first edge of the distal side wall 2220 of the axially successive second ratchet pocket 220 by a connecting wall 2230 which extends, for example, axially or substantially axially.

The first edge of the proximal side wall 2210 of one second ratchet pocket 220 is arranged further away from the distal end 200D of the piston rod 20 than the second edge of the proximal side wall 2210 of the same second ratchet pocket 220, such that the proximal sidewall 2210 is inclined with respect to the longitudinal axis in plan view of the second ratchet pocket 220 and the piston rod 20. The distal side wall 2220 of the second ratchet pocket 220 may be essentially perpendicular to the longitudinal axis.

The piston rod 20 has a second protrusion 260. The protrusion 260 extends axially. The second protrusion 260 may form a second channel 270 in cooperation with the axial row of second ratchet pockets 220. The second ratchet pockets 220 form bulges of the second channel 270. For example, the channel 270 is bound in the second angular direction by the second ratchet pockets 220 of the axial row and the connecting walls between axially successive second ratchet pockets 220. The channel 270 may be bound in the first angular direction by the second protrusion 260.

The channels 240 and 270 are expediently separated from one another, for example by means of the ridge, such that a passover from one of the channels in an angular direction into the other one of the channels is prevented.

The second ratchet pockets 220 may be axially offset with respect to the first ratchet pockets 210. In particular, one, and in particular only one, second ratchet pocket 220 may be axially positioned between two axially successive first ratchet pockets 210. In other words, the axial row of first ratchet pockets 210 and the axial row of second ratchet pockets may be arranged out of phase.

The piston rod 20 may have a further row of first ratchet pockets 210, which preferably forms a further channel 240 in cooperation with a further first protrusion 230. The piston rod 20 additionally or alternatively may have a further row of second ratchet pockets 220, which preferably forms a further channel 270 in cooperation with a further second protrusion 260. For example, the piston rod 20 has a twofold rotational symmetry with respect to the longitudinal axis. One of the first protrusions 230 and one of the second protrusions 260 in each case may, for example, be comprised by a single web protruding from a side surface of the piston rod.

FIG. 10B shows a side view of a variant of the piston rod according to FIG. 10A.

In the present variant, in contrast to the piston rod 20 of FIG. 10A, both the distal sidewalls 2110, 2210 and the proximal sidewalls 2120, 2220 are oblique with respect to the longitudinal axis. In the present variant, the second edge of the distal sidewall 2110 or 2210 of one first or second ratchet pocket 210 or 220 is closer to the distal end 200D of the piston rod 20 than the first edge of the respective distal side wall 2110 or 2210. Thus, an undercut is formed in each of the first and second ratchet pockets 210, 220. The undercut is directed in distal direction and preferably in the first angular direction. This design may be advantageous for reliably retaining a respective pawl element in engagement with the respective ratchet pocket.

Figure 4A:
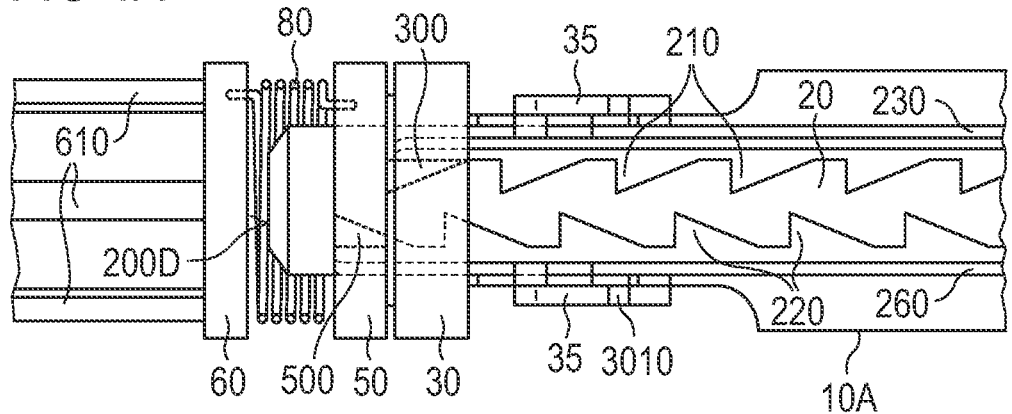
FIG. 4A shows a partial side view of the drive assembly according to the second exemplary embodiment in a start configuration.

FIG. 4A shows a partial side view of the drive assembly according to the second exemplary embodiment. In order to simplify the illustration, the exterior housing 10B, the push button 40, and the detachable member 70 are omitted in FIG. 4A and also in the subsequent FIGS. 4B through 6B. The spring 80 is cut open in FIGS. 4A through 6B to improve the view onto the piston rod 20.

In the configuration illustrated in FIG. 4A, the drive assembly is in a start configuration, for example in a configuration ready for setting a dose, in particular a first dose. When the drive assembly is in the start configuration, the piston rod 20 may, for example, be in a proximal start position with respect to the housing. For dispensing a dose, the piston rod 20 may be advanced in the distal direction with respect to the housing away from the proximal start position. In FIG. 4A, the drive member 30 is in a rest position, which may be, for example, a position closest or essentially closest to the distal end 100D of the housing 10A, 10B.

The drive member 30 has a pawl element 300. The pawl element 300 is in particular configured for engaging the first ratchet pockets 210 of one of the axial rows of first ratchet pockets for forming a first interlock. The first interlock is configured for blocking proximal axial movement of the piston rod 20 with respect to the drive member 30. In one embodiment, the pawl element 300 has the inverse shape of a first ratchet pocket 210. In the start configuration, the pawl element 300 of the drive member 30 is in engagement with one first ratchet pocket 210.

The drive member 30 may, for example, be designed as a drive sleeve through which the piston rod 20 extends. The pawl element may protrude radially inwardly from an inner surface of the drive member towards the piston rod. In particular, it protrudes into the channel 240 formed by one of the first protrusions 230 and one of the axial rows of first ratchet pockets 210.

The stop member 50 also has a pawl element 500. The pawl element 500 of the stop member 50 is in particular configured for engaging the second ratchet pockets 220 of one of the axial rows of second ratchet pockets for forming a second interlock. The second interlock is configured for blocking proximal axial movement of the piston rod 20 with respect to the housing 10A, 10B. In one embodiment, the pawl element 500 of the stop member 50 has the inverse shape of a second ratchet pocket 220. In the start configuration, the pawl element 500 of the stop member 50 is in engagement with one second ratchet pocket 220.

The stop member 50 may, for example, be designed as a sleeve through which the piston rod 20 extends. The pawl element 500 of the stop member 50 may protrude radially inwardly from an inner surface of the drive member towards the piston rod 20. In particular, the pawl element 500 of the stop member 50 protrudes into the channel 270 formed by one of the second protrusions 260 and one of the axial rows of second ratchet pockets 220.

The drive member 30 and the stop member 50 each may have a further pawl element for interacting with the second axial row of first ratchet pockets and second ratchet pockets, respectively.

Figure 4B:
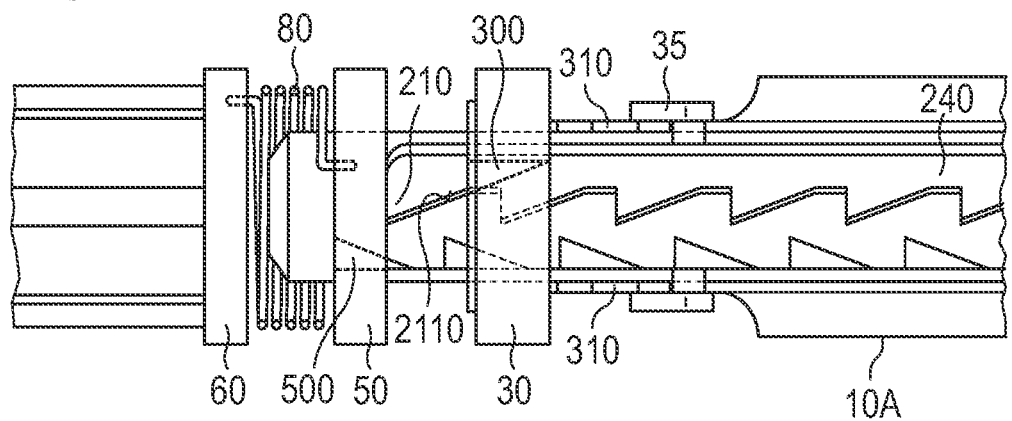
FIG. 4B shows a partial side view of the drive assembly according to the second exemplary embodiment in a first drive mode configuration, e.g. in a configuration during setting of a dose.

FIG. 4B shows a partial side view of the drive assembly according to the second embodiment in a first drive mode configuration, for example during setting of a dose.

In the first configuration, compared to the start configuration as illustrated in FIG. 4A, the drive member 30 is proximally displaced with respect to the housing 10A, 10B towards a dose set position. For proximally displacing the drive member 30 for setting the dose, the push button 40 may be moved in the proximal direction with respect to the housing. Proximal movement of the push button 40 is transferred to the drive member 30 by means of interaction of the push button 40 with the lever 35 and interaction of the lever 35 with the drive member 30, as described above. The drive member 30 may be rotationally fixed with respect to the housing 10A, 10B in the present embodiment, such that it is only axially displaced with respect to the housing 10A, 10B when being moved in the proximal direction.

The drive member 30 interacts with the piston rod 20 to convert proximal axial movement of the drive member 30 with respect to the housing 10A, 10B for setting the dose into rotational movement of the piston rod 20 in a first rotational direction towards the second angular position. In particular, during movement of the drive member 30 in the proximal direction, pawl element 300 interacts with that first ratchet pocket 210 with which the pawl element 300 has been engaged in the start configuration to rotate the piston rod 20 in the first rotational direction. For example, pawl element 300 is pressed against the inclined proximal sidewall 2120 of said first ratchet pocket 210 such that the proximal movement of the drive member 30 with respect to the piston rod 20 is converted into rotational movement of the piston rod 20 in the first rotational direction with respect to the housing 10A, 10B.

In this way, the pawl element 300 of the drive member 30 disengages from the first ratchet pocket 210 such that is movable to a proximally subsequent first ratchet pocket 210 through the channel 240, which channel 240 is defined by the first axially extending protrusion of the piston rod 20 in cooperation with the axial row of first ratchet pockets 210. Preferably, for setting the dose, the pawl element 300 of the drive member 30 moves from one first ratchet pocket 210 through the channel 240 which is defined by the first axial protrusion 230 in cooperation with the axial row of first ratchet pockets 210 to the proximally successive first ratchet pocket 210.

Due to the second interlock formed by interaction of the stop member 50 with the piston rod 20, proximal movement of the piston rod 20 with respect to the housing 10A, 10B is blocked. In particular, proximal movement of the piston rod 20 with respect to the housing is prevented by engagement of the pawl element 500 of the stop member 50 with one of the second ratchet pockets 220. Thus, the piston rod does not follow the drive member 30 in the proximal direction when the drive member 30 is proximally displaced, for example for setting the dose. Consequently, the dose accuracy may be increased as the piston rod 20 is reliably held in a stable position during dose setting.

However, when the piston rod 20 is rotated in the first rotational direction by means of interaction with the drive member 30, it carries the stop member 50 with it. Engagement of the pawl element 500 of the stop member 50 with the second ratchet pocket 220 is promoted by rotation of the piston rod 20 in the first rotational direction, for example by means of the second ratchet pocket 220 tapering in the second rotational direction, opposite to the first rotational direction.

The reset member 60 is rotationally fixed with respect to the housing 10A, 10B when the drive assembly is in the drive mode. For example, the reset member 60 is rotationally locked with respect to the detachable member 70 by means of interaction of the tooth element 610 with the indentation 710. The detachable member 70 may, in turn, be rotationally locked with respect to the housing 10A, 10B—in particular with respect to the exterior housing 10B—when the drive assembly is in the drive mode. The joint between the detachable member 70 and the housing 10A, 10B may be releasable, for example it may be designed as a threaded or a bayonet connection.

Since one end of the spring 80 is fixed to the reset member 60 and an opposite end of the spring 80 is fixed to the stop member 50, rotational movement of the stop member 50 with respect to the housing 10A, 10B—and thus also with respect to the reset member 60—deforms the spring 80. In particular, the end of the spring 80 which is fixed to the stop member 50 is rotationally displaced with respect to that end of the spring 80 which is fixed to the reset member 60. The spring 80 expediently tends to resume its undeformed shape. The spring 80 may act as torsion spring. Alternatively or additionally, spring 80 may be a compression spring. Spring 80 may be a coil spring, preferably a helical coil spring.

The deformation of the spring increases a resilient bias acting on the stop member 50 in the second rotational direction. By interaction of the stop member 50, in particular of the pawl element 500 of the stop member 50, with the second ratchet pocket 220 of the piston rod, the resilient bias is transferred to the piston rod such that the piston rod is also resiliently biased in the second rotational direction. Thus, the piston rod 20 is rotated in the first rotational direction with respect to the housing 10A, 10B against the resilient bias generated by the spring 80 and transferred to the piston rod 20 by means of the stop member 50. The stop member 50 therefore functions also as a rotational bias member. Alternatively, a separate rotational bias member may be provided.

Figure 4C:
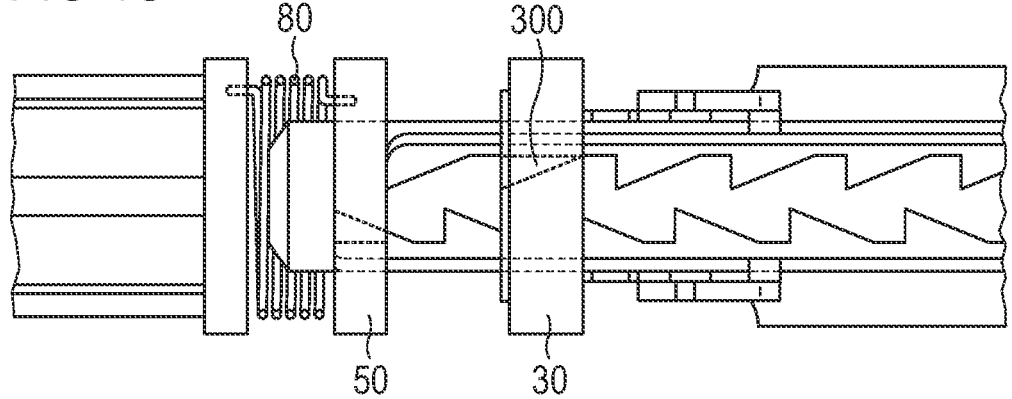
FIG. 4C shows a partial side view of the drive assembly according to the second exemplary embodiment in a second drive mode configuration, e.g. in a dose set configuration.

FIG. 4C shows the drive assembly according to the second exemplary embodiment in a second drive mode configuration, for example in a dose set configuration.

In the dose set configuration, the drive member 30 is displaced further in the distal direction as compared with the configuration of FIG. 4B. In the dose set configuration, the drive member 30 may be in the dose set position, which is, for example, an axial position into which the drive member may be moved and which may be closest or substantially closest to the proximal end of the drive assembly.

When the drive member 30 has been moved to the dose set position, its pawl element 300 laterally overlaps with a first ratchet pocket 210, which first ratchet pocket 210 is proximally subsequent to the first ratchet pocket 210 with which the pawl element 300 engaged in the start configuration, such that the pawl element 300 of the drive member 30 can engage said first ratchet pocket 210.

The drive assembly may be configured for dispensing fixed doses in this case. For example, the first ratchet pocket 210 with which the pawl element 300 of the drive member 30 laterally overlaps when the drive member is in the dose set position, may be the first ratchet pocket 210 which directly succeeds the first ratchet pocket 210 with which the pawl element 300 engages in the start configuration.

It is also conceivable that the pawl element 300 of the drive member is moved past the proximally directly successive first ratchet pocket 210 and further in the proximal direction to another first ratchet pocket 210 for engaging with that first ratchet pocket 210 during setting of the dose. In this case, the drive assembly may be configured for dispensing variable doses. The amount of drug of one dose may, for example, be selectable in steps determined by the axial distance between the distal side walls 2110 of two directly subsequent first ratchet pockets 210.

By means of the resilient bias, the stop member 50 and the piston rod 20 are rotated in the second rotational direction, towards first angular position of the piston rod 20, such that the pawl element 300 of the drive member 30 is brought into engagement with the proximally subsequent first ratchet pocket 210. Thus, during setting the dose, the piston rod 20 is rotated in the second rotational direction with respect to the housing 10A, 10B and the drive member 30 by means of the resilient bias subsequently to the rotation in the first rotational direction.

Before the pawl element 300 of the drive member 30 may engage the (next) first ratchet pocket 210, rotation of the piston rod 20 and the stop member 50 in the second rotational direction is prevented by mechanical cooperation of the pawl element 300 of the drive member 30 and the connecting wall 2130, which may be arranged between two first ratchet pockets 210 (see, for example, FIG. 10A). When the pawl element 300 of the drive member 30 may engage the (next) first ratchet pocket 210, the resilient bias decreases and drives rotation of the piston rod 20 and, in particular, of the stop member 50 in the second rotational direction such that the pawl element 300 of the drive member 30 engages the (next) first ratchet pocket 210.

When the pawl element 300 of the drive member 30 is in engagement with the first ratchet pocket 210, further rotation of the piston rod 20 in the second rotational direction with respect to the housing 10A, 10B is blocked since the drive member 30 is rotationally locked with respect to the housing 10A, 10B. In this way, the drive member 30 limits the angular range of motion of the piston rod 20 in the second angular direction.

In a drive assembly having the piston rod 20 as illustrated and described above in connection with FIG. 10B, during setting of the dose, the drive member 30 is proximally displaced until the pawl element 300 has passed the distal sidewall 2110 of one proximally subsequent ratchet pocket. Rotation of the piston rod 20 in the second rotational direction brings the pawl element 300 of the drive member 30 into partial engagement with said first ratchet pocket 210. Subsequently, full engagement of the pawl element 300 of the drive member 30 with the first ratchet pocket 30 may be achieved by a, preferably small, distal displacement of the drive member 30 with respect to the piston rod 20 and the housing 10A, 10B. Said distal displacement may be driven by further rotation of the piston rod 20 in the second rotational direction by means of the resilient bias.

For dispensing the set dose, the drive member 30 is distally displaced with respect to the housing, in particular from the dose set position towards the rest position. The drive member is, in particular, only axially moved during dispensing of the dose.

FIG. 5A shows a partial side view of the drive assembly according to the second exemplary embodiment in a third drive mode configuration, e.g. a configuration during dispensing of the set dose.

For dispensing the set dose, the drive member 30 interacts with the piston rod 20 to displace the piston rod 20 in the distal direction with respect to the housing 10A, 10B. In particular, the first interlock blocks proximal movement of the piston rod 20 with respect to the drive member 30 and, accordingly, it blocks distal movement of the drive member 30 with respect to the piston rod 20, such that the drive member 30 carries the piston rod 20 with it in the distal direction. For example, the pawl element 300 of the drive member 30 is pressed against the distal sidewall 2110 of the first ratchet pocket 210 for transferring distal movement of the drive member 30 to the piston rod 20.

During dispensing of the dose, the piston rod 20 is preferably only axially moved in the distal direction. In particular, the piston rod 20 is not rotated with respect to the housing 10A, 10B during dispensing of the set dose.

Distal movement of the piston rod 20 is converted to rotational movement of the stop member 50 in the first rotational direction by means of interaction of the axial row of second ratchet pockets 220 with the pawl element 500 of the stop member 50. In particular, when dispensing the set dose, the pawl element 500 of the stop member 50 disengages one second ratchet pocket 220, such that it is displacable through the channel 270, which is defined by the second axial extending protrusion 260 and the second ratchet pockets 220, towards a proximally subsequent second ratchet pocket 220. Preferably, the distal movement of the piston rod 20 and the rotational movement of the stop member 50 result in a relative movement of the pawl element 500 of the stop member 50 with respect to the piston rod 20 from one second ratchet pocket 220 through the channel 270 to the proximally successive second ratchet pocket 220. By means of the rotational movement of the stop member 50 in the first rotational direction with respect to the housing 10A, 10B and, in particular, with respect to the piston rod 20, the first and second ends of the spring 80 are rotationally displaced with respect to each other, such that the resilient bias on the stop member is increased.

FIG. 5B shows a partial side view of the drive assembly according to the second exemplary embodiment in a fourth drive mode configuration, e.g. a dose dispensed configuration.

In the fourth drive mode configuration, the pawl element 500 of the stop member 50 is rotated into engagement with the proximally subsequent second ratchet pocket 220 by means of the resilient bias after the piston rod 20 has been distally displaced to a position where the distal sidewall 2210 of said second ratchet pocket 220 has passed the pawl element 500 of the stop member 50. The drive assembly may be designed such that engagement and/or disengagement of the pawl element 300, 500 of the drive member 30 and the stop member 50, respectively, produces audible and/or tactile feedback for the dose-set and the dose-dispense operation, respectively.

When the pawl element 500 of the stop member 50 is in full engagement with the second ratchet pocket 220, further rotation of the stop member 50 in the first rotational direction may be prevented by interaction with the housing 10A, 10B, in particular via the piston rod 20 and the drive member 30. In this way, the angular range of motion of the stop member 50 in the first rotational direction with respect to the housing 10A, 10B is limited.

In a drive assembly which comprises a piston rod according to the variant described in connection with FIG. 10B, the pawl element 500 of the stop member 50 may, at first, be brought into partial engagement with the second ratchet pocket 220, in particular such that the pawl element 500 is still disengaged from the undercut. For example when the user releases the push button 40 after dispensing the dose, the pawl element 500 of the stop member is subsequently brought into full engagement with the second ratchet pocket 220 of the piston rod by a further rotation of the stop member 50 in the second rotational direction. The further rotation of the stop member 50 in the second rotational direction may be converted into a proximal movement of the piston rod 20 with respect to the housing—in particular by means of interaction of the pawl element 50 with the second ratchet pocket 220—, the piston rod carrying the drive member 30 and, in particular, the push button 40 with it in the proximal direction. In this way, the drive assembly may be operable to reduce pressure of the piston rod 20 on the piston of a cartridge.

The drive assembly may be operable for dispensing a plurality of doses. The piston rod 20 may be movable from the proximal start position to a distal end position, for example by repeating dose-set and dose-dispense operations as described above in connections with FIGS. 4A to 5B, until the drive assembly is in a fully dispensed configuration. In the fully dispensed configuration, the last available dose of drug may have been delivered from a cartridge which a drug delivery device may comprise in addition to the drive assembly.

When the drive assembly is in the fully dispensed configuration, the last-dose-stop element 250 may interact with the drive member 30 to block further distal movement of the piston rod 20 with respect to the housing and/or to block proximal movement of the drive member 30 with respect to the piston rod 20.

For example, the drive member 30 is in the rest position when the drive assembly is in the fully dispensed position and is in particular inoperable to move substantially further in the distal direction from the rest position with respect to the housing 10A, 10B. The last-dose-stop element 250 of the piston rod 20 may, for example, abut the drive member 30 on the proximal side of the drive member 30 for blocking further distal movement of the piston rod 20. Alternatively or additionally, pawl element 300 of the drive member 30 may abut a proximal end of the channel 240 defined by the first axially extending protrusion 230 and the first ratchet pockets 210. Thus, proximal movement of the drive member 30 with respect to the piston rod 20 may be blocked as well. Since proximal movement of the piston rod 20 with respect to the housing 10A, 10B is blocked by the second interlock formed by means of interaction of the piston rod 20 with the stop member 50, proximal movement of the drive member 30 with respect to the housing 10A, 10B is blocked in the fully dispensed configuration.

The push button 40 is coupled to the drive member 30 via the lever 35. In this way, also proximal movement of the push button 40 for setting a further dose is blocked in the fully dispensed position.

Accordingly, if it is intended to reuse the drive assembly, e.g. for dispensing drug from a different cartridge, it is necessary to reset the drive assembly. For resetting the drive assembly, it may be switched from the drive mode to a reset mode. During switching from the drive mode to the reset mode, the first interlock—formed by interaction of the drive member 30 with the axial row of first ratchet pockets 210—and the second interlock—formed by an interaction of the stop member 50 with the axial row of second ratchet pockets 220—are unlocked.

For unlocking the second interlock, the reset member 60 is rotated in the first rotational direction with respect to the housing 10A, 10B. Rotation of the reset member 60 may, for example, be driven by a rotation of the detachable member 70, similarly as described above in connection with FIG. 3 and with the first embodiment.

The rotational movement of the reset member 60 in the first rotational direction is transferred to the stop member, in particular by means of the spring 80, such that the stop member is also rotated in the first rotational direction with respect to the housing 10A, 10B, as well. When rotating the reset member 60 in the first rotational direction, the spring 80 may generate a reverse bias acting on the stop member 50, the reverse bias being in particular directed in the opposite rotational direction than the resilient bias transferred to the stop member 50 in the drive mode. By means of the reverse bias, the stop member 50 is resiliently biased in the first rotational direction for promoting rotational movement of the stop member 50 in the first rotational direction.

The stop member 50 may be resiliently biased in the second rotational direction when the drive assembly is in the drive mode, in particular when the drive assembly is in the fully dispensed mode. In this case, for unlocking the second interlock, the resilient bias in the second rotational direction is released by means of rotational displacement of the reset member 60, before the reverse bias is generated by further rotational displacement of the reset member 60.

The second interlock may, in particular, be unlocked by disengaging the pawl element 500 of the stop member 50 from one of the second ratchet pockets 220. Preferably, the pawl element 500 of the stop member 50 is displaced out of the second ratchet pocket 220 but remains engaged with the channel 250 which is defined by the second axially extending protrusion 260 and the second ratchet pockets 220.

FIG. 6A shows a partial side view of the drive assembly according to the second embodiment in a configuration during switching the drive assembly from the drive mode to the reset mode. In the configuration of FIG. 6A the second interlock is unlocked while the first interlock is still locked. The first interlock may be unlocked subsequently to unlocking the second interlock during switching the drive assembly from the drive mode to the reset mode.

For unlocking the first interlock, the reset member 60 may, for example, be rotated further in the first rotational direction. By means of the reverse bias generated by the spring 80, the rotation of the reset member 60 is transferred to the stop member 50 such that the stop member 50 is rotated further in the first rotational direction with respect to the housing.

During its further rotational movement in the first rotational direction, the stop member 50 may interact with the piston rod 20 to carry the piston rod 20 with it in the first rotational direction. For example, the pawl element 500 of stop member 50 is pressed against the second axially extending protrusion 260 for rotating the piston rod 20 in the first rotational direction.

Since the drive member 30 is rotationally locked with respect to the housing 10A, 10B, the rotation of the piston rod 20 in the first rotational direction with respect to the housing 10A, 10B is also a rotation of the piston rod 20 in the first rotational direction with respect to the drive member 30. In particular, one of the first ratchet pockets of the piston rod may be rotated out of engagement with the pawl element 300 of drive member 30 by rotation of the piston rod 20 with respect to the drive member 30 in the first rotational direction.

The drive member 30 may limit the angular range of motion of the piston rod 20 in the first rotational direction, for example by means of interaction of its pawl element 300 with the first axially extending protrusion 230 of the piston rod 20. In turn, the angular range of motion of the stop member 50 in the first rotational direction with respect to the housing 10A, 10B may be limited, for example by means of interaction with the housing 10A, 10B via the second protrusion 260 of the piston rod 20 and the drive member 30.

FIG. 6B shows the drive assembly according to the second exemplary embodiment in the reset mode. In the reset mode, the first and second interlocks are unlocked.

By means of the reverse bias generated by the spring 80, the piston rod 20 and the stop member 50 may be biased in the first rotational direction with respect to the housing 10A, 10B. The reverse bias may expediently be countered by means of interaction of the piston rod 20 and the stop member 50 with the housing 10A, 10B when the drive assembly is in the reset mode. In particular, the reverse bias may be countered by means of engagement of the stop member 50 with the piston rod 20, engagement of the piston rod 20 with the drive member 30, and engagement of the drive member 30 with the housing 10A, 10B. It is also conceivable that the piston rod 20 and the stop member 50 are unbiased when the drive assembly is in the reset mode. Thus, the piston rod 20 and the stop member 50 expediently do not rotate when the drive assembly is in the reset mode. Thus, the pawl element 300 of the drive member 30 remains disengaged from the first ratchet pockets 210 when the drive assembly is in the reset mode. In addition, the pawl element 500 of the stop member 50 remains disengaged from the second ratchet pockets of the piston rod 20 when the drive assembly is in the reset mode.

At the end of its rotational travel for switching the drive assembly from the drive mode to the reset mode, the reset member 60 may engage a detent in the housing 10A, 10B for locking the reset member 60 rotationally with respect to the housing 10A, 10B while the drive assembly is in the reset mode. In this way, the reverse bias may be easily retained, for example when the detachable member 70 is disconnected from the housing 10A, 10B. This reduces the danger that the first and second interlocks may accidentally resume their locked configuration when the drive assembly is in the reset mode.

The unlocked first and second interlocks allow the piston rod 20 to be moved in the proximal direction with respect to housing 10A, 10B, stop member 50, and drive member 30. The piston rod 20 can be pushed back to its proximal start position by a user of the drive assembly, for example. The piston rod can also be moved towards the proximal start position when the detachable member 70 is reconnected to the housing, for example. In particular, the piston rod 20 may be pushed towards the proximal start position by interaction with the piston of a cartridge containing drug, which cartridge may be comprised by the detachable member 70 when the detachable member 70 is re-connected to the housing 10A, 10B.

For switching the drive assembly from the reset mode to the drive mode, the reset member 60 may be rotated in the second rotational direction with respect to the housing 10A, 10B. The rotational movement can be driven by means of interaction with the detachable member 70, for example when connecting the detachable member 70 to the housing 10A, 10B.

By means of the rotational movement of the reset member 60 in the second rotational direction with respect to the housing, the resilient bias on the stop member 50 in the second rotational direction is restored, in particular after having removed the reverse bias. The resilient bias drives a rotational movement of the stop member 50 in the second rotational direction with respect to the housing 10A, 10B and the piston rod 20. In this way, the second interlock is locked by re-engaging the pawl element 500 of stop member 50 with one of the second ratchet pockets 220 of the piston rod.

When the second interlock is locked, the stop member 50 transfers the resilient bias in the second rotational direction to the piston rod 20, such that the piston rod 20 is (resiliently) rotated in the second rotational direction with respect to the drive member 30. In this way, pawl member 300 of drive member 30 is brought into engagement with one of the first ratchet pockets 210, such that the first interlock is locked subsequent to locking the second interlock.

FIG. 7 shows a sectional side view of a variant of the resettable drive assembly according to the second exemplary embodiment.

In this variant, the push button is of multipart construction, comprising a cap part 40A and a sleeve part 40B. The cap part 40A may be positioned such that it closes a proximal opening of the sleeve part 40B. The cap part 40A and the sleeve part 40B may be permanently locked to each other during operation.

The piston rod 20 may be designed in the same fashion as described above for the second exemplary embodiment in connection with FIGS. 10A and 10B. In FIG. 7 the piston rod 20 is illustrated in a position which is rotated by approximately 90° around its longitudinal axis as compared to the side view of FIG. 10A. The bearing 20B of the piston rod 20 is cut open in FIG. 7 to allow viewing the main body 20A in the region of the bearing 20B.

Figure 8A:
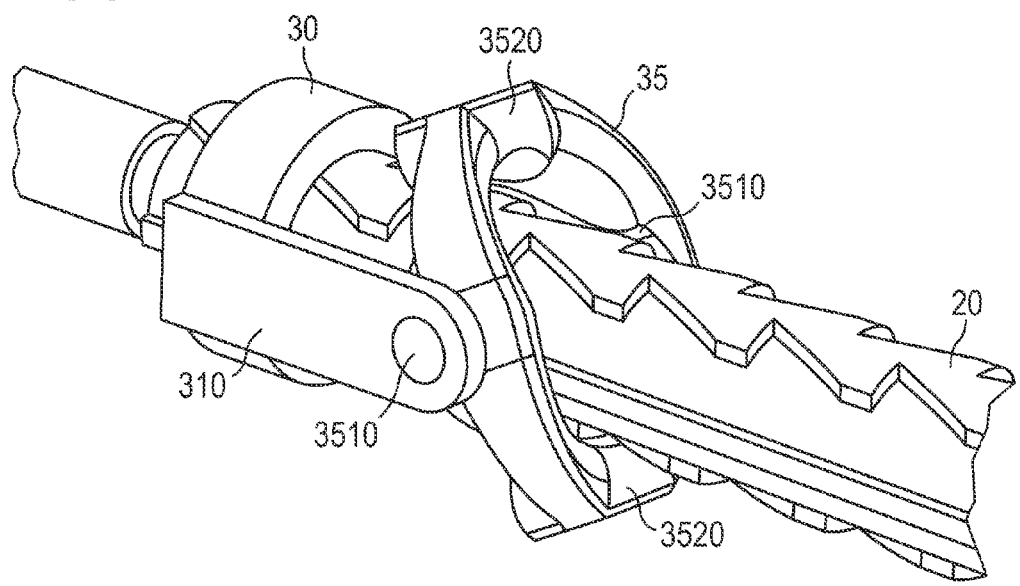
FIG. 8A shows an oblique view of the drive member, lever and piston rod of the drive assembly according to FIG. 7.

FIG. 8A shows an oblique view of the drive member, the lever and the piston rod of the drive assembly according to the variant of the second embodiment.

The lever 35 is designed in the form of a ring in the present variant, in particular the lever may be a single part component. A single part lever 35 may be particularly strong, robust and stiff. The lever 35 may extend basically completely to the internal dimensions of the exterior housing 10B so that it has a particular high mechanical stability.

The lever 35 may comprise journal bearings 3510, in particular on opposing sides, for engaging mating holes or indentations of the drive member 30. The journal bearings 3510 may be designed in the form of pins. Each journal bearing 3510 expediently engages a hole in an axial arm 310 of the drive member 30. It is also conceivable that the drive member comprises journal bearings 3010 for engaging mating features like holes in the lever 35, as described in connection with the second embodiment above.

Figure 8B:
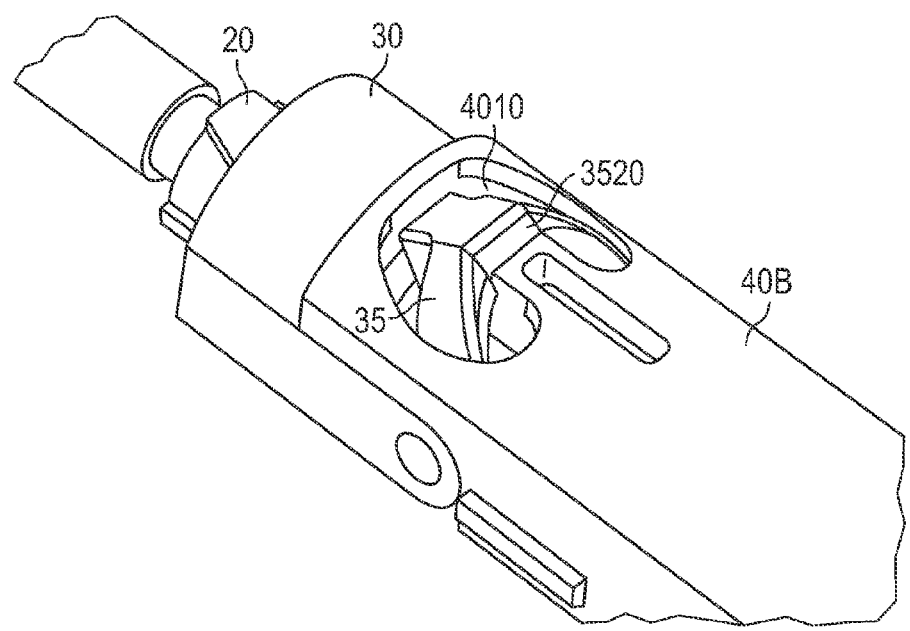
FIG. 8B shows an oblique view of the drive member, the lever and the push button of the drive assembly according to FIG. 7.

FIG. 8B shows an oblique view of the drive member 30, the lever 35 and the sleeve part 40B of the push button 40 of the drive assembly according to the variant of the second embodiment.

The sleeve part 40B comprises the moving pivot 4010 comprising a slot. The lever 35 has a drive region 3520 provided for engaging with the slot of the moving pivot 4010. In particular, the lever 35 is rotatable around the moving pivot by means of engagement of the drive region 3520 with the slot 4010.

The lever 35 comprises a further drive region 3520 for engaging the fixed pivot 1010. The fixed pivot 1010 is formed by the pivot part 10A in cooperation with a protrusion of the exterior housing 10B in the present variant.

In addition to the pivot part 10A and the exterior housing 10B, the housing additionally comprises a connection part 10C in the present embodiment (see FIG. 7). The connection part 10C may be axially and rotationally fixed with respect to exterior housing 10B and pivot part 10A. The drive assembly according to the present variant may be configured for forming a releasable bayonet connection between the detachable member 70 and the housing, in particular with the connection part 10C. Connection part 10C may comprise the female part of the bayonet connector. Alternatively, the releasable connection may be a thread connection as in the second embodiment, for example. In the drive mode, the detachable member 70 is connected to the housing by means of the bayonet connection such that it is axially and rotationally locked with respect to the housing 10A, 10B, 10C.

In the present variant, the reset member has a set of dog-teeth 620 configured for interacting with the housing 10A, 10B, 10C. The dog-teeth 620 are in particular configured for engaging with mating indentations 120 of the housing, in particular of the connection part 10C. The reset member 60 is axially displaceable with respect to the housing 10A, 10B, 10C such that the dog-teeth 620 are engageable with and disengageable from the indentations 120 of the housing 10B. The spring 80 may generate a resilient bias in the distal direction on the reset member 60 for promoting engagement of the dog-teeth 620 with the mating indentations 120. For example the spring 80 is a compression spring which is also configured for being torsionally elastically deformed, i.e. the spring may be a combined compression spring and torsion spring.

Figure 9A:
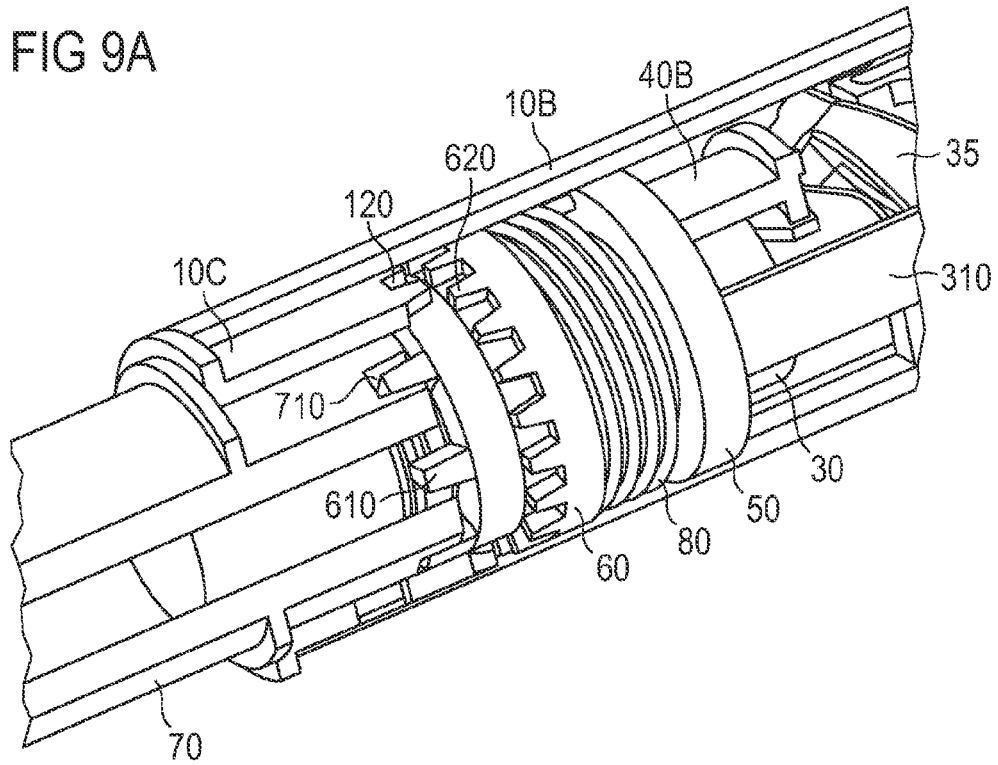
FIG. 9A shows an oblique sectional view of the drive assembly of FIG. 7 in the drive mode.

FIG. 9A shows an oblique sectional view of the drive assembly according to FIG. 7 in the drive mode. The drive assembly is configured for performing dose-set and dose-dispense operations as described above in connection with the second embodiment.

When the drive assembly is in the drive mode, axially oriented tooth-elements 610 of the reset member 60 engage respective indentations 710 of the detachable member 70. In this way, the reset member 60 is rotationally coupled to, in particular rotationally locked with respect to, the detachable member 70 and the housing 10A, 10B, 10C.

In the drive mode, the distal resilient bias on the reset member 80 may be countered by the engagement of the detachable member 70 with the housing 10A, 10B, 10C. The detachable member 70 may interact with the reset member 60 to retain the dog-teeth 620 disengaged from the indentations of the housing 10B when the drive assembly is in the drive mode. Thus, the dog-teeth 620—contrary to the tooth-elements 610—are inoperable to block rotational movement of the reset member 60 in the drive mode.

The detachable member 70 may represent a cartridge holder for a cartridge of a drug delivery device in one embodiment. The reset member 60 may be operable to interact with the cartridge to axially and/or rotationally lock the cartridge in the cartridge holder 70. In particular, the drive assembly is configured such that the distal resilient bias generated by the spring 80 on the reset member 60 is transferred to the cartridge. The detachable member 70 and the cartridge may be, for example, configured such that the cartridge prevents full engagement of the tooth elements 610 with the indentations 710 of the detachable member 70 when the cartridge is positioned in the detachable member 70. For example, a proximal end of the cartridge may be arranged in an axial position between the proximal end of the detachable member 70 and the bottom of the indentations 710 of the detachable member 70 when the drive assembly is in the drive mode. In this case, the tooth-elements 610 of reset member 60 may be held in abutment with the proximal end of the cartridge by means of the distal resilient bias for locking the cartridge in the detachable member 70.

For switching the drive assembly from the drive mode to the reset mode, the detachable member 70 is detached from the housing 10A, 10B, e.g. by unlocking the bayonet connection. Subsequently, the detachable member 70 is distally removed from the housing 10A, 10B.

For unlocking the bayonet connection, the detachable member 70 is rotated in the first rotational direction with respect to the housing 10A, 10B. By means of interaction of the indentations 710 of the detachable member 70 with the tooth-elements 610 of the reset member 60, the detachable member 70 carries the reset member 60 with it in the first rotational direction for unlocking the first and second interlocks by means of interaction with the stop member 50 and the piston rod 20, in particular via the spring 80, as described above in connection with FIGS. 6A and 6B of the second embodiment. During rotation of the detachable member 70 for unlocking the bayonet connection, the dog-teeth 620 of the reset member 60 remain disengaged from the mating indentations 120 of the connection part 10C.

Subsequently, the detachable member 70 is distally displaced for removing the detachable member 70 from the housing 10A, 10B, 10C. Accordingly, the detachable member 70 no longer counteracts the distal resilient bias exerted on the reset member 60 by the spring 80. Thus, the resilient bias may now drive a distal movement of the reset member, in particular for engaging the dog-teeth 620 with the mating indentations 120 of the connection part 10C.

Figure 9B:
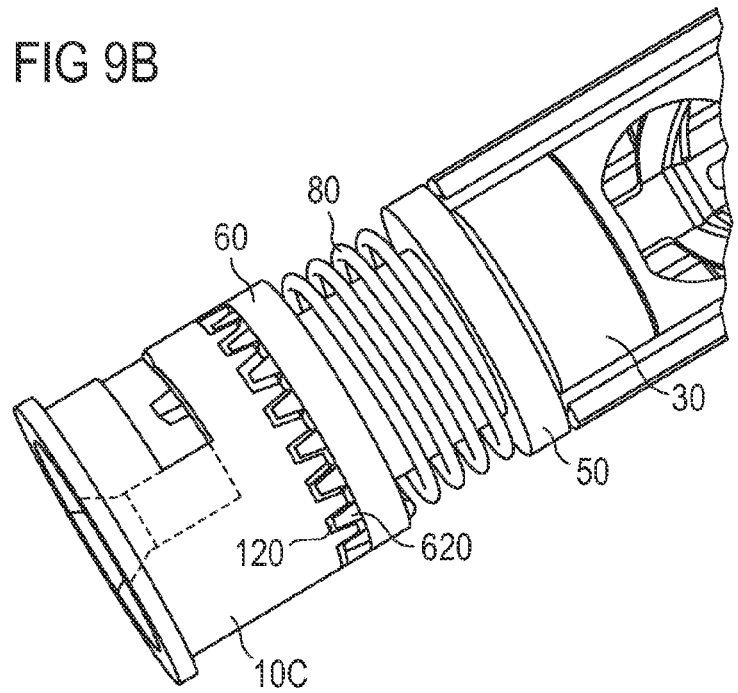
FIG. 9B shows an oblique sectional view of the drive assembly of FIG. 7 in the reset mode.

FIG. 9B shows the drive assembly in the reset mode after the detachable member 70 has been removed.

In the reset mode, the dog-teeth 620 are in engagement with the indentations 120 of the housing 10C such that the reset member is rotationally locked with respect to the housing. Advantageously, in this way, the first and second interlocks are reliably retained unlocked when the drive assembly is in the reset mode.

For switching the drive assembly from the reset mode to the drive mode, the detachable member 70 is pressed against the reset member 60 in the proximal direction when the bayonet connection between the detachable member 70 and the housing 10A, 10B, 10C is established. The proximal movement of the detachable member 70 is transferred to the reset member 60, such that the dog-teeth 620 are disengaged from the indentations 120 of the housing 10C against the distal resilient bias.

Subsequently, the detachable member 70 is rotated in the second rotational direction with respect to the housing 10A, 10B for locking the bayonet connection. By means of engagement of the tooth elements 610 of the reset member 60 with the indentations 710 of the detachable member, the rotational movement of the detachable member 70 is transferred to the reset member 60 for locking the first and second interlocks in the same fashion as described above in connection with the second embodiment.

Figure 11:
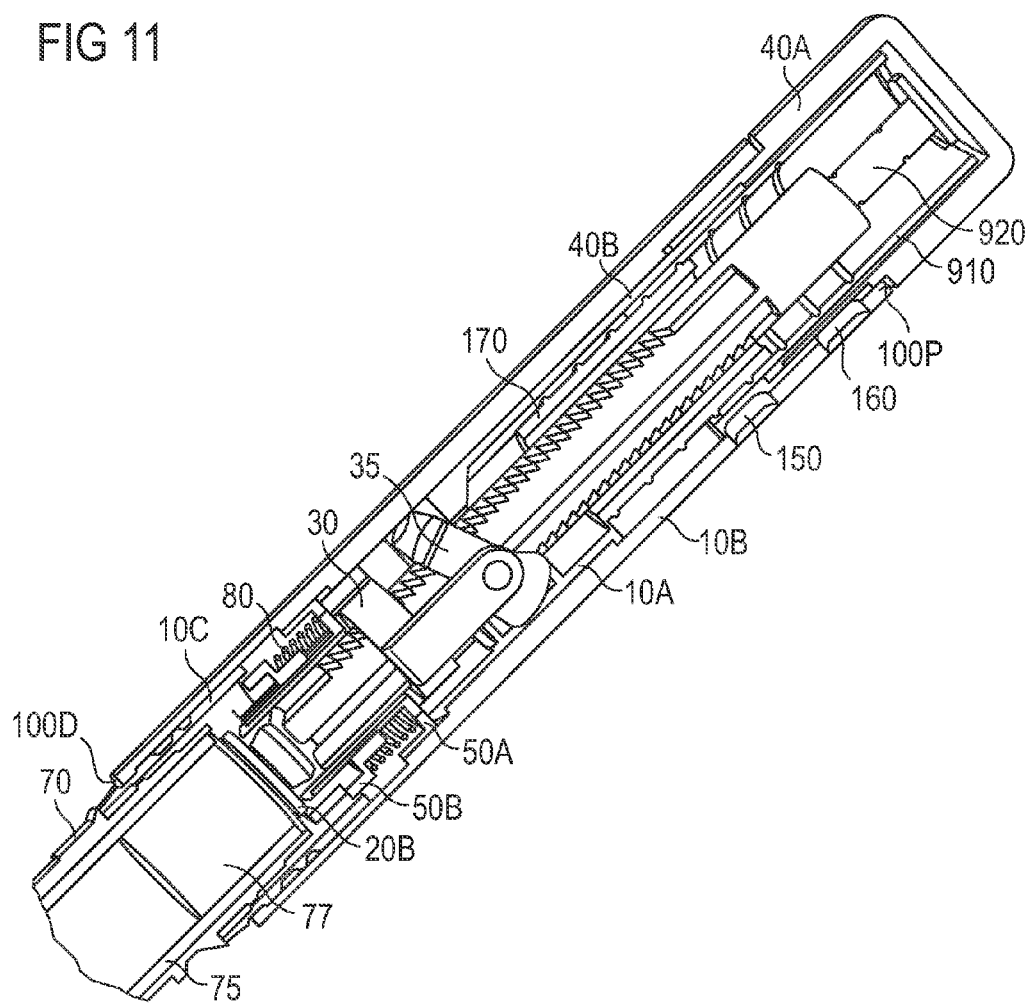
FIG. 11 shows an oblique sectional view of a drug delivery device according to one embodiment.

FIG. 11 shows an oblique sectional view of a drug delivery device according to one embodiment.

The drug delivery device has a drive assembly comprising a housing with a proximal end 100P and a distal end 100D. The housing has a pivot part 10A and an exterior housing 10B, as in the previous embodiments. Similarly to the variant of the second embodiment, it has a separate connection part 10C at its distal end, which connection part 10C is locked axially and rotationally with respect to the exterior housing 10B and with respect to the pivot part 10A. Alternatively, the connection part 10C may be integrated in the pivot part 10A or the exterior housing 10B. The drive assembly also has a detachable member 70. The drive assembly may be configured for forming a releasable connection, e.g. a threaded connection, between the detachable member 70 and the connection part 10C.

The detachable member 70 may be a cartridge holder operable to retain a cartridge 75 comprising a piston 77, which is expediently movable with respect to the cartridge 75 for dispensing drug from the cartridge 75. A piston rod 20 comprised by the drive assembly may be moveable from a proximal start position to a distal end position. The piston rod 20 may be configured for distally displacing the piston 77. The piston rod is, for example, designed as described above in connection with FIG. 10B.

The drive assembly may further comprise a drive member 30 for distally displacing the piston rod towards the distal end position, a lever 35 and a push button 40A, 40B. The drive member, the lever 35 and the push button may be designed as described above in connection with the variant of the second embodiment of the drive assembly, for example, in connection with FIGS. 8A and 8B. Contrary to the second embodiment, the central axis of the lever 35 through the journal bearings 3510 does not bisect the lever arm between the fixed pivot 1010 and the moving pivot 4010 to achieve a mechanical advantage of 2:1. Rather, the journal bearings may for example be positioned closer to the fixed pivot 1010 than to the moving pivot 4010, in particular such that a mechanical advantage of 3:1 is achieved.

The drug delivery device may have an operation indicator assembly. The operation indicator assembly may be provided for displaying a first information to the user when the drug delivery device is in a dose-set configuration and a second information, different from the first information, when the drug delivery device is in a configuration ready for setting a dose. The first and second information each may comprise a symbol. For example, the first information comprises an arrow pointing in the distal direction and the second information comprises an arrow pointing in the proximal direction. The operation indicator may comprise a set window 160 in the housing, in particular in the exterior housing 10B, for displaying the first and second information. Subregions of the push button 40 may be provided with the first information and the second information, respectively, and may be alternatingly visible through the set window 160 for displaying the first information and the second information.

The drug delivery device may comprise a dose indicator assembly, preferably a dose counter assembly. The dose indicator assembly may comprise an indicator member, in particular an indicator sleeve 910. The indicator sleeve 910 may be axially displaceable with respect to the housing and/or rotatable with respect to the housing around the longitudinal axis extending between the proximal end 100P and the distal end 100D.

The dose indicator assembly may additionally comprise an indicator rod 920. The indicator rod 920 is preferably axially and rotationally locked with respect to the indicator sleeve 910.

Figure 12:
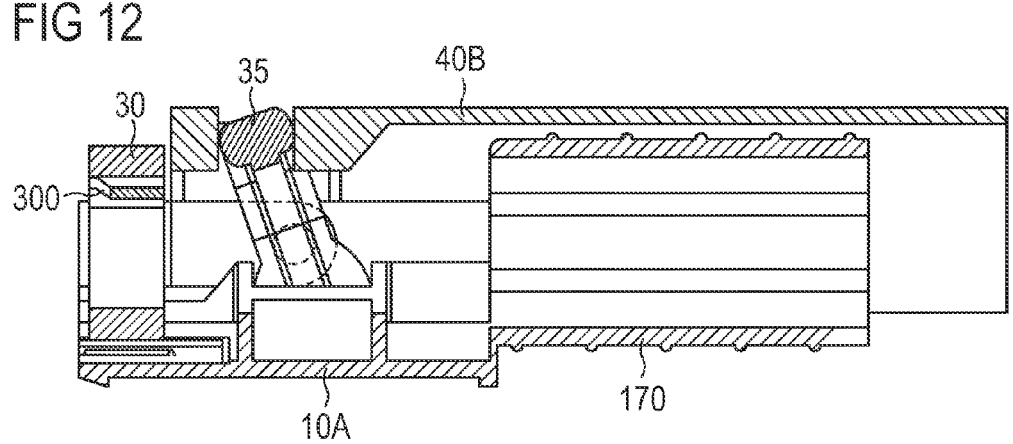
FIG. 12 shows a sectional view of the push button, the lever and the pivot part of the drug delivery device according to FIG. 11.

FIG. 12 shows a sectional view of the pivot part 10A of the drug delivery device, together with the sleeve part 40B of the push button 40 and the lever 35.

Figure 13:
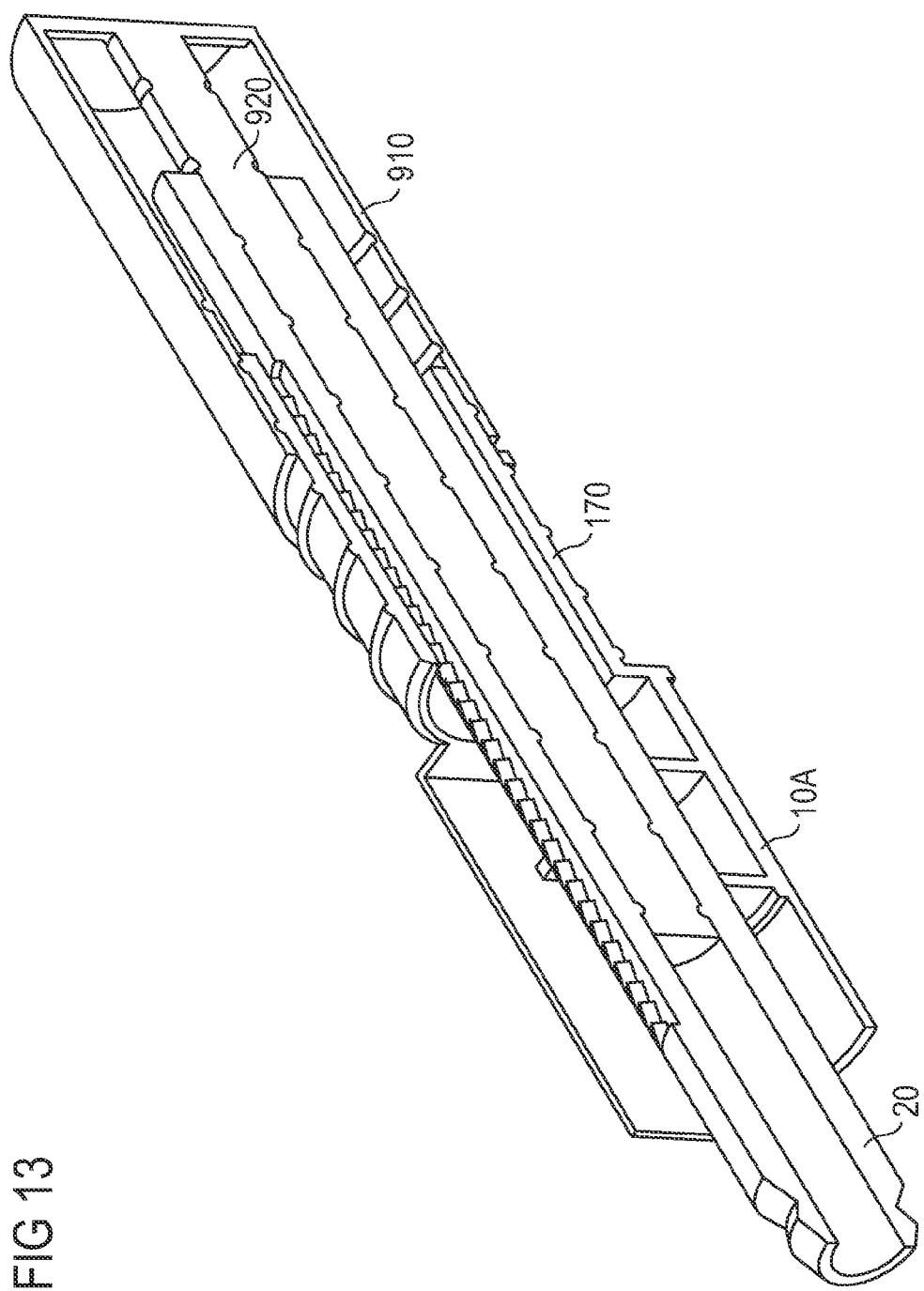
FIG. 13 shows an oblique sectional view of the piston rod, the pivot part and the dose counter of the drug delivery device according to FIG. 11.

FIG. 13 shows an oblique sectional view of the piston rod 20, the pivot part 10A, the indicator sleeve 910 and the indicator rod 920 of the drug delivery device.

The pivot part 10A comprises a thread element 170. The thread element 170 may have an external thread, the external thread may in particular be a non self-locking thread. The indicator sleeve 910 may be threadedly connected to the thread element 170, preferably such that a non self-locking thread connection is formed between the indicator sleeve 910 and the thread element 170. By means of interaction with the thread element 170, the indicator sleeve 910 may be operable to perform a helical motion within the exterior housing 10B.

The indicator rod 920 may be axially locked with respect to the piston rod 20 and rotatable with respect to the piston rod 20. For example, the piston rod 20 may be designed in a tubular fashion. The indicator rod 920 may partially extend within the piston rod. The piston rod 20 may have one or more ring-like protrusions on an inner surface. The ring-like protrusion(s) preferably protrude radially inwardly from the inner surface. The indicator rod 920 may have one or more ring-like notches. The ring-like notch(es) may extend radially inwardly in an outer surface of the indicator rod 920. The ring-like protrusion(s) of the piston rod 20 may be operable to engage the ring-like notch(es).

In a variant, an additional, in particular non self-locking, thread connection may exist between the piston rod 20 and the indicator rod 920 in addition to the thread connection between the thread element 170 and the indicator sleeve 910. If the additional thread connection is non self-locking then the thread connection between the thread element 170 and the indicator sleeve 910 may be of a self locking type. If the thread connection between the thread element 170 and the indicator sleeve 910 is non self-locking then the additional thread connection may be of a self locking type.

The drive assembly may, for example, be configured such that distal movement of the piston rod with respect to the housing is converted into rotational movement of the indicator rod 920 with respect to the piston rod and a helical movement of the indicator sleeve 910 with respect to the housing 10A, 10B, 10C by means of the interaction of the indicator rod 920 with the piston rod 20 and the thread element 170. For example, when one dose is dispensed, the indicator sleeve 910 is rotationally displaced with respect to the housing 10A, 10B, 10C and the piston rod 20 by 30°.

Further, the dose indicator assembly may comprise a dose window 150 in the exterior housing 10B. A subregion of an outer surface of the indicator sleeve 910 may be visible through the dose window 150. For example, the indicator sleeve 910 is provided with symbols, such as numbers. The dose indicator assembly may be configured for sequentially displaying the symbols through the dose window 150. The drug delivery device may, in particular, be configured for dispensing a plurality of doses—preferably fixed doses, i.e. pre-set and non-user variable doses—of a drug from the cartridge 75. The dose indicator assembly is expediently configured for displaying dose related information, e.g. the number of doses which have been dispensed from and/or which are remaining in the cartridge 75.

Figure 14A:
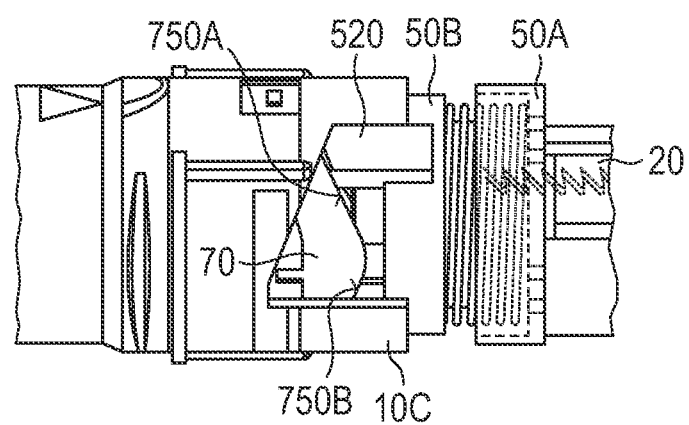
FIG. 14A shows a partial side view of the drug delivery device in a start configuration.

FIG. 14A shows a partial side view of the drug delivery device in a start configuration, e.g. a configuration ready for setting a dose.

The drug delivery device has a stop member 50 comprising a first part 50A and a second part 50B. The first part 50A and the second part 50B are rotationally locked with respect to each other. The first part 50A and the second part 50B are expediently rotatable with respect to the housing 10A, 10B, 10C. The housing, for example the connection part 10C, may be operable to limit the angular range of rotational movement of the stop member 50A, 50B with respect to the housing 10A, 10B, 10C in the first and/or second rotational direction.

Expediently, the first part 50A and the second part 50B are axially displaceable with respect to each other. The drug delivery device may be operable to convert axial movement of the second part 50B with respect to the first part 50A and with respect to the housing 10A, 10B, 10C into rotational movement of the stop member 50, in particular of first part 50A, with respect to the housing 10A, 10B, 10C.

The first part 50A may be a sleeve. The second part 50B may be a sleeve, preferably a ring. The expression "ring" preferably denotes a short(er) sleeve. The sleeve 50A may extend through the ring 50B. The ring 50B may have at least one axially extending slot, which may, in particular, be guided by a mating axially extending protrusion of the first part 50A for coupling the first and second parts 50A, 50B in a rotationally locked and axially displaceable fashion.

The first part 50A may be axially locked with respect to the housing 10A, 10B, 10C. The first part 50A may comprise a pawl element 500 for forming the unlockable second interlock by interaction with the row or one of the rows of second ratchet pockets 220 as described above in connection with the second embodiment of the drive assembly. In particular, the stop member 50A, 50B is configured as a rotational bias member also in the present embodiment.

The drug delivery device comprises a spring 80 which interacts with the first part 50A and the second part 50B of the stop member for resiliently biasing the second part 50B of the stop member in the distal direction with respect to the first part 50A and the housing 10A, 10B, 10C. When the drug delivery device is in the drive mode, the drug delivery device may be operable to convert the distal resilient bias acting on the second part 50B into a rotational bias of the first part 50A in the second rotational direction. Alternatively or additionally, the drug delivery device may be operable to convert the distal resilient bias acting on the second part 50B into a rotational bias acting on the first part 50A in the first rotational direction when the drug delivery device is in the reset mode.

For example, the second part 50B may be provided with a pin 520. The pin 520 may, for example, protrude distally from the second part 50B. The pin 520 may interact with, e.g. bear on, a first diverter element. The first diverter element may comprise or be formed by a first ramp 750A. The first ramp 750A may be provided by the detachable member 70, for example. The first ramp 750A may be inclined such that the second part 50B is deflected in the second rotational direction when it moves distally along the first ramp 750A.

In the start configuration as illustrated in FIG. 14A, the pin 520 may be locked with respect to rotational movement in the second rotational direction by means of interaction with the housing 10A, 10B, 10C. For example, the pin 520 may abut a side face of the connection part 10C, in particular a side face of an indentation 120 of the connection part 10C, such that further rotational movement in the second rotational direction is prevented. Additionally or alternatively, further rotational movement in the second rotational direction of the pin 520 may be prevented by means of interaction of the stop member 50A, 50B with the housing 10A, 10B, 10C via the first part 50B, the piston rod 20, and the drive member 30.

For setting a dose, the drive member 30 is distally displaced from the rest position to a dose set position, such that it disengages one first ratchet pocket 210 of the piston rod and subsequently engages a proximally subsequent ratchet pocket 210 as described above in connection with FIGS. 4A-4C. When disengaging from the first ratchet pocket 210, the drive member 30 rotates the piston rod 20 in the first rotational direction against the resilient bias. When rotating in the first rotational direction, the piston rod 20 carries the stop member 50A, 50B with it in the first rotational direction. The first ramp 750A deflects the second part 50B of the stop member in the proximal direction when the second part 50B moves along the first ramp 750A in the first rotational direction. In this way, the spring 80 is compressed and the distal resilient bias acting on the second part 50B is increased.

Figure 14B:
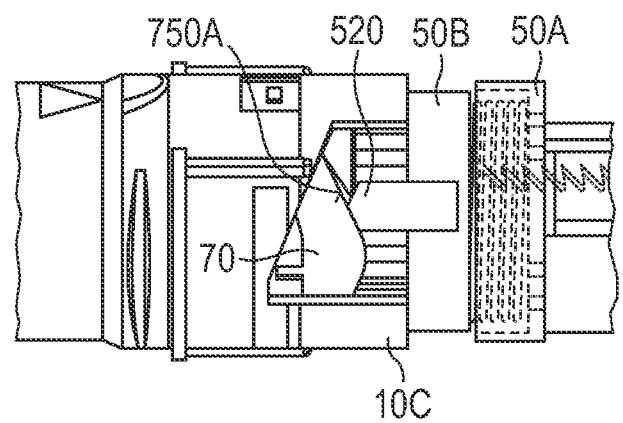
FIG. 14B shows a partial side view of the drug delivery device in a first drive mode configuration, e.g. a dose set configuration.

FIG. 14B shows a partial side view of the drug delivery device in a configuration during setting of a dose, after the piston rod 30 has been rotationally displaced in the first rotational direction.

Subsequently, the piston rod 30 is rotated in the second angular direction by means of the resilient bias. More precisely, when the drive member 30 is in an axial position where its pawl element 300 can engage the subsequent first ratchet pocket 210, the distal resilient bias acting on the stop member 50A, 50B generated by the spring 80 is no longer counteracted by interaction of the pawl element 300 with the piston rod 20. Thus, the distal resilient bias may drive a distal movement of the second part 50B of the stop member with respect to the housing 10A, 10B, 10C along the first ramp 750A. By means of the pin 520 of the second part 50B interacting with the first ramp 750A, the second part 50B is deflected in the second rotational direction when the second part 50B moves distally. The second part 50 B carries the first part 50A of the stop member and the piston rod 20 with it in the second rotational direction. When the pawl element 300 of the drive member 30 is fully engaged with the subsequent first ratchet pocket 210, the pin 520 may have returned to the start position as illustrated and described in connection with FIG. 14A.

Analogously, during dispensing of the set dose, the stop member 50A, 50B is rotated in the first rotational direction against the resilient bias with respect to the housing 10A, 10B, 10C and the piston rod 20, such that the pawl element 500 of the first part 50A disengages one second ratchet pocket 220 of the piston rod 20. When the first and second parts 50A, 50B of the stop member move in the first rotational direction, the pin 520 of the second part 50B is deflected by the first ramp 750A such that it is displaced in the proximal direction with respect to the housing 10A, 10B, 10C and the first part 50A. By means of the proximal displacement of the second part 50B, the spring 80 is compressed and the distal resilient bias is increased.

Subsequently, the stop member 50A, 50B is rotated in the second rotational direction with respect to the housing 10A, 10B, 10C and the piston rod 20 by means of the distal resilient bias, which is converted into a rotational bias in the second rotational direction by means of the first ramp 750A, such that the pawl element 50 of the first part 50A engages a proximally subsequent second ratchet pocket 220 of the piston rod 20. The piston rod 20 itself is only axially displaced with respect to the housing 10A, 10B, 10C during dispensing of the dose, as described above in connection with FIGS. 5A and 5B.

Figure 15A:
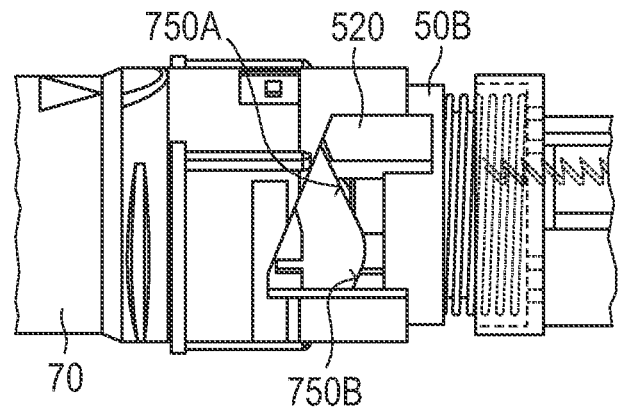
FIG. 15A shows a partial side view of the drug delivery device in a fully dispensed configuration.

FIG. 15A shows a partial side view of the drug delivery device in a fully dispensed configuration.

In the fully dispensed configuration, proximal and/or distal movement of the piston rod 20 may be blocked as described above in connection with the second embodiment of the drive assembly. Like in the start position, rotational movement of the pin 520 in the second rotational direction with respect to the housing 10A, 10B, 10C may be blocked in the fully dispensed configuration by means of interaction with the housing.

For switching the drug delivery device from the drive mode to the reset mode, the detachable member 70 may be detached from the housing 10A, 10B, 10C. For example, the detachable member is unscrewed from the connection part 10C.

When detaching the detachable member 70 from the housing 10A, 10B, 10C, the detachable member is rotated in the second rotational direction with respect to the connection part 10C such that the whole first ramp 750A is passed along the pin 520 in the second rotational direction. When the detachable member 70 is rotated in the second rotational direction, a proximal end of the first ramp 750A may approach the pin 520. Subsequently, the proximal end of the first ramp 750B may be moved past the pin 520 in the second rotational direction.

Figure 15B:
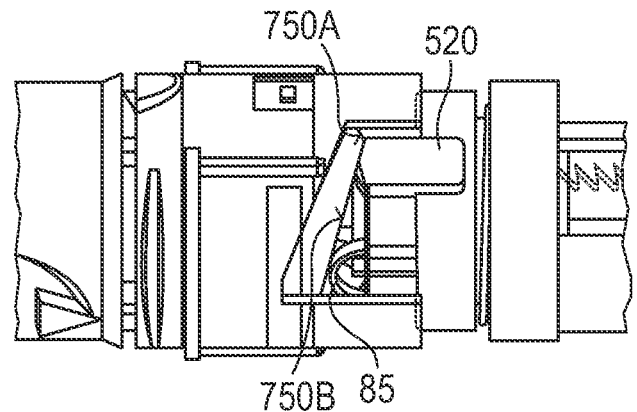
FIG. 15B shows a partial side view of the drug delivery device in a first configuration during switching from the drive mode to the reset mode.

FIG. 15B shows a partial side view of the drug delivery device in a first configuration during switching from the drive mode to the reset mode. In the first configuration, the proximal end of the first ramp 750A has been moved past the pin 520 in the second rotational direction.

When the proximal end of the first ramp 750A has been moved past the pin 520, the pin 520 may bear on a second ramp 750B. In the present embodiment, the second ramp 750B is comprised by the detachable member 70. However, it may be also comprised by the housing, for example by the connection part 10C. The second ramp 750B may be inclined such that the second part 50B is deflected in the first rotational direction when it is moved distally along the second ramp 750B by means of the distal resilient bias generated by the spring 80.

Figure 15C:
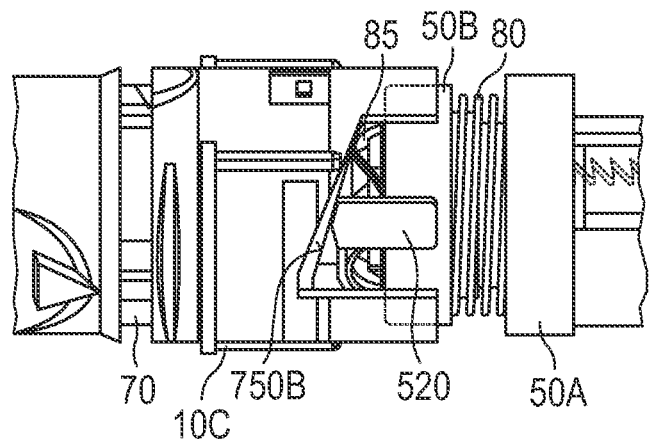
FIG. 15C shows a partial side view of the drug delivery device in a second configuration during switching from the drive mode to the reset mode.

FIG. 15C shows a partial side view of the drug delivery device in a second configuration during switching from the drive mode to the reset mode. In the second configuration according to FIG. 15C, the second part 50B of the stop member has been distally displaced with respect to the first part 50A compared to the first configuration according FIG. 15B by means of the distal resilient bias generated by the spring 80.

During the distal movement, the second part 50B is deflected in the first rotational direction by means of interaction of its pin 520 with the second ramp 750B. Thus, the stop member is rotated in the first rotational direction for unlocking the second interlock which is formed by the stop member 50A, 50B and the piston rod 20 and, preferably, for subsequently unlocking the first interlock which is formed by the piston rod 20 and the drive member 30. Unlocking of the first and second interlocks is achieved by rotational displacement of the stop member 50A, 50B with respect to the piston rod 20 and of the piston rod 20 with respect to the drive member 30 as described above in connection with FIGS. 6A and 6B. When the first and second interlocks are unlocked, the drive assembly is in the reset mode.

Figure 15D:
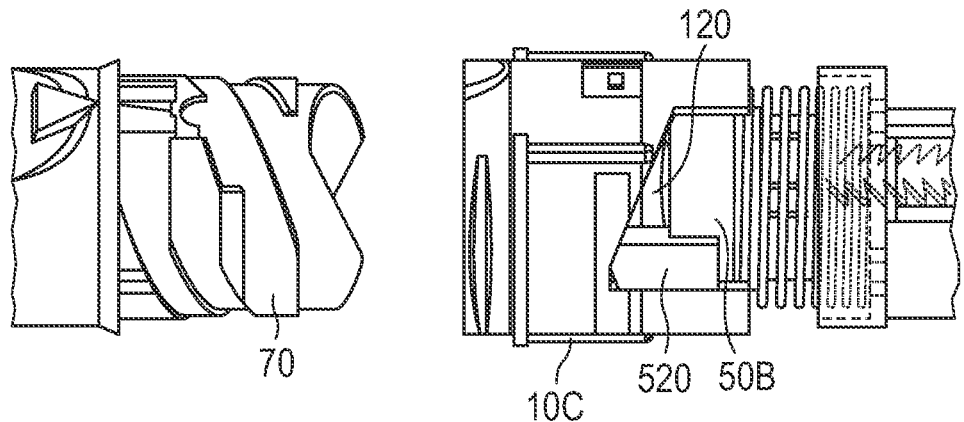
FIG. 15D shows a partial side view of the drug delivery device in the reset mode.

FIG. 15D shows a partial side view of the drug delivery device in the reset mode.

In the reset mode, the second part 50B of the stop member may be operable to interact with the housing for rotationally locking the stop member 50A, 50B with respect to the housing 10A, 10B, 10C. For example, the pin 520 is held in engagement with an indentation 120 of the connection part 10C by means of the distal resilient bias, the resilient bias being in particular be generated by the spring 80. By means of engagement of the pin 520 with the indentation 120 further rotational movement of the stop member 50A, 50B in the first rotational direction with respect to the housing 10A, 10B, 10C may be blocked. For blocking rotational movement in the first rotational direction, the pin 520 may abut a side face of the indentation 120 which side face may in particular be opposite to the side face which the pin 520 abuts in the start configuration (see FIG. 14A). Preferably, also rotation in the second rotational direction with respect to the housing 10A, 10B, 10C is blocked by means of engagement of the pin 520 with the indentation 120. For example, the indentation 120 may have a ramped bottom face which is configured to bias the pin 520 in the first rotational direction with respect to the connection part 10C in cooperation with the distal resilient bias generated by the spring 80. In this way, the drug delivery device may be expediently retained in the reset mode while the detachable member 70 is disconnected from the housing 10A, 10B, 10C.

In the reset mode, the piston rod may be returned, e.g. pushed back into the start position. Afterwards, the drug delivery device may be switched back to the drive mode.

Figure 16A:
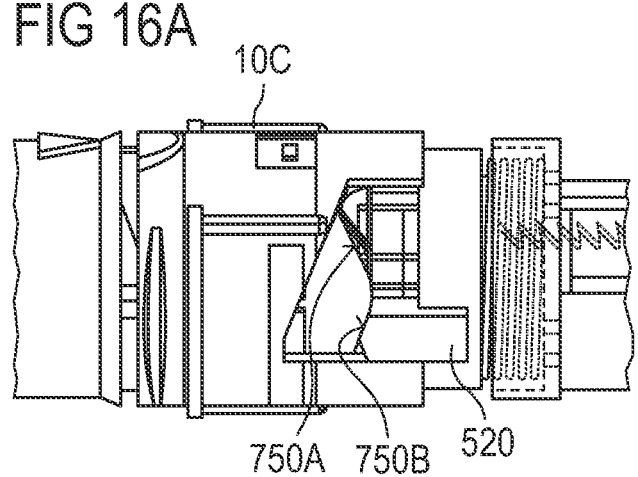
FIG. 16A shows a partial side view of the drug delivery device in a first configuration during switching from the reset mode to the drive mode.

FIG. 16A shows a partial side view of the drug delivery device in a first configuration during switching from the reset mode to the drive mode. For switching the drug delivery device from the reset mode to the drive mode, the detachable member 70 is re-connected to the housing 10A, 10B, 10C.

When establishing the connection, the pin 520 bears on the second ramp 750B. The detachable member is rotated in the first rotational direction, such that the proximal end of the second ramp 750B approaches the pin 520 and subsequently moves past the pin 520 in the first rotational direction. When the proximal end of the second ramp 750B approaches the pin 520, the pin is proximally displaced such that the spring 80 is compressed and the axial resilient bias on the second part 50B of the stop member increases.

Figure 16B:
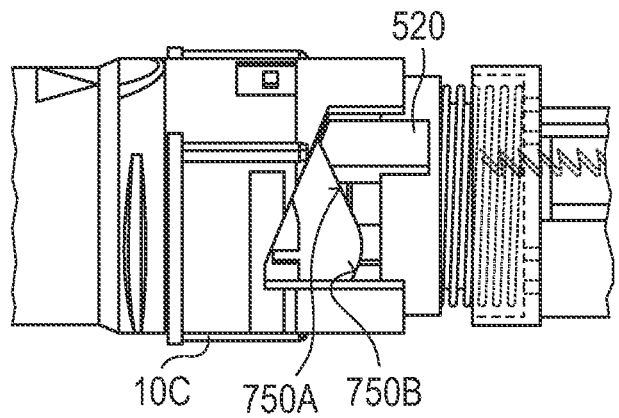
FIG. 16B shows a partial side view of the drug delivery device in a second configuration during switching from the reset mode to the drive mode.

FIG. 16B shows a partial side view of the drug delivery device in a second configuration during switching from the reset mode to the drive mode.

In the second configuration, the pin 520 bears on the first ramp 750A after the proximal end of the second ramp 750B has been moved past the pin 520 in the first rotational direction. The distal resilient bias promotes rotation of the stop member 50A, 50B in the second rotational direction as described above in connection with FIGS. 14A and 14B. In this way, the distal resilient bias drives a rotation of the stop member in the second rotational direction for subsequently locking the second interlock and, thereafter, the first interlock. In particular, the drug delivery device may return to the start configuration as illustrated in FIG. 14A when the detachable member 70 is fully engaged with the housing 10A, 10B, 10C.

The drug delivery device may have a further spring 85 (see, for example, FIGS. 15B and 15C) for locking the cartridge 75 in the detachable member 70. The further spring may be fixed on a distal end of the first part of the stop member 50A, for example. The further spring 85 may have the form of a crown, in particular having a plurality of elastically deformable lobes. The further spring 85 may be a spring washer, for example. When the drug delivery device is in the drive mode, the cartridge 75 may deform the lobes such that the further spring 85 generates a resilient bias on the cartridge for locking the cartridge 75 in the detachable member 70.

The invention is not restricted to the exemplary embodiments by the description on the basis of said exemplary embodiments. Rather, the invention encompasses any new feature and also any combination of features, which in particular comprises any combination of features in the patent claims and any combination of features in the exemplary embodiments, even if this feature or this combination itself is not explicitly specified in the patent claims or exemplary embodiments.

The invention claimed is:

1. A resettable drive assembly for a drug delivery device comprising
    a housing having a proximal end and a distal end;
    a piston rod being rotatable with respect to the housing and being axially displaceable with respect to the housing between a proximal start position and a distal end position;
    a drive member for distally displacing the piston rod towards the end position when dispensing a dose; and
    a stop member;
    wherein the drive assembly is configured such that
    the drive member is operable to interact with the piston rod for forming an unlockable first interlock, the first interlock being operable to block proximal movement of the piston rod with respect to the drive member;
    the stop member is operable to interact with the piston rod for forming an unlockable second interlock, the second interlock being operable to block proximal movement of the piston rod with respect to the housing;
    when the drive assembly is in a drive mode, the first and second interlocks are locked such that proximal movement of the piston rod from the end position to the start position is prevented by the first interlock and the second interlock;
    for switching the drive assembly from the drive mode to a reset mode, the piston rod is rotatable with respect to the drive member for unlocking the first interlock and the stop member and the piston rod are rotatable with respect to each other for unlocking the second interlock; and
    when the drive assembly is in the reset mode, the first interlock and the second interlock are unlocked such that proximal movement of the piston rod to the start position is allowed.

2. The resettable drive assembly of claim 1, wherein the drive member is axially displaceable with respect to the housing and rotationally locked with respect to the housing.

3. The resettable drive assembly of claim 1, wherein the stop member is axially and rotationally locked with respect to the housing.

4. The resettable drive assembly of claim 3, being configured such that the first interlock and the second interlock are unlockable by a rotation of the piston rod from a first angular position to a second angular position with respect to the housing.

5. The resettable drive assembly of claim 1, wherein the stop member is rotatable with respect to the housing.

6. The resettable drive assembly of claim 5, being configured such that the second interlock is unlockable by a rotation of the stop member in a first rotational direction with respect to the housing and the piston rod.

7. The resettable drive assembly of claim 6, wherein, when the second interlock is unlocked, the stop member is operable to interact with the piston rod such that the piston rod follows further rotational movement of the stop member in the first rotational direction with respect to the housing and the drive member for unlocking the first interlock.

8. The resettable drive assembly of claim 7, wherein the piston rod has a substantially axially extending protrusion, the substantially axially extending protrusion being operable to limit the angular range of motion of the stop member in the first rotational direction with respect to the piston rod.

9. The resettable drive assembly of claim 6, further comprising a spring, the spring interacting with the stop member to generate a resilient bias on the stop member for promoting rotation of the stop member in a second rotational direction, opposite to the first rotational direction, with respect to the housing when the drive assembly is in the drive mode and the spring interacting with the stop member to generate a resilient bias on the stop member for promoting rotation of the stop member in the first rotational direction with respect to the housing for unlocking the first interlock and the second interlock when switching the drive assembly to the reset mode.

10. The resettable drive assembly of claim 9, wherein
    the stop member has a first part which is axially locked with respect to the housing and a second part which is axially displaceable with respect to the housing and resiliently biased in a first axial direction by means of the spring,
    the drive assembly has a first diverter element and is configured for converting axial movement of the second part in the first axial direction into rotational movement of the stop member in the second rotational direction by means of interaction of the second part with the first diverter element when the drive assembly is in the drive mode, and
    the drive assembly has a second diverter element and is configured for converting axial movement of the second part in the first axial direction into rotational movement of the stop member in the first rotational direction by means of interaction of the second part with the second diverter element when switching the drive assembly to the reset mode.

11. The resettable drive assembly of claim 10, wherein the drive assembly has a first ramp and a second ramp, each ramp having a proximal end and a distal end, the proximal ends of the first and second ramps face each other, and the second part bears on the first ramp when the assembly is in the drive mode and the second part bears on the second ramp when switching the drive assembly to the reset mode.

12. The resettable drive assembly of claim 9, further comprising a reset member being releasably engageable with the housing, the reset member being operable to retain the drive assembly in the reset mode when it is engaged with the housing, wherein the spring is operable to generate a resilient bias in an axial direction on the reset member for locking the reset member in engagement with the housing when the drive assembly is in the reset mode.

13. A drug delivery device comprising the resettable drive assembly of claim 12, further comprising a detachable member for connecting to the housing, the detachable member being one of a cartridge and a cartridge holder, wherein the detachable member is operable to interact with the reset member such that, when connecting the detachable member to the housing, the engagement of the reset member with the housing is released against the resilient bias on the reset member and, when disconnecting the detachable member from the housing, the reset member is brought into engagement with the housing by means of the resilient bias on the reset member.

* * * * *